US008983279B2

(12) United States Patent
Adair et al.

(10) Patent No.: US 8,983,279 B2
(45) Date of Patent: Mar. 17, 2015

(54) VOLATILE MATERIAL DISPENSER AND METHOD OF EMITTING A VOLATILE MATERIAL

(75) Inventors: Joel E. Adair, Racine, WI (US); Imre J. Dancs, Greenfield, WI (US); Brian T. Davis, Burlington, WI (US); Miguel A. Esparza, Mexico City (MX); Kamran Faterioun, New Berlin, WI (US); Tracy L. Guard, Milwaukee, WI (US); Sebastian D. Hasik, Antioch, IL (US); Dirk K. Nickel, Mukwonago, WI (US); Jesse Richard, Racine, WI (US); Christopher R. Sheridan, Racine, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 333 days.

(21) Appl. No.: 13/562,975

(22) Filed: Jul. 31, 2012

(65) Prior Publication Data
US 2014/0034748 A1 Feb. 6, 2014

(51) Int. Cl.
 *A61L 9/02* (2006.01)
 *A61L 9/03* (2006.01)
 *H05B 1/02* (2006.01)
(52) U.S. Cl.
 CPC .............. *A61L 9/037* (2013.01); *H05B 1/0225* (2013.01); *A61L 9/02* (2013.01)
 USPC ............................ 392/395; 392/403; 239/136
(58) Field of Classification Search
 CPC ......... A61L 9/02; A61L 9/037; H05B 1/0225
 See application file for complete search history.

(56) References Cited

U.S. PATENT DOCUMENTS

| 3,288,556 | A | | 11/1966 | Weber, III |
| 4,251,714 | A | | 2/1981 | Zobele |
| 4,771,563 | A | | 9/1988 | Easley |
| 4,874,924 | A | | 10/1989 | Yamamoto et al. |
| 5,038,394 | A | | 8/1991 | Hasegawa et al. |
| 5,175,791 | A | * | 12/1992 | Muderlak et al. ............. 392/390 |
| 5,222,186 | A | | 6/1993 | Schimanski et al. |
| 5,647,053 | A | | 7/1997 | Schroeder et al. |
| 5,940,577 | A | | 8/1999 | Steinel |
| 6,446,384 | B2 | | 9/2002 | Pedrotti et al. |

(Continued)

FOREIGN PATENT DOCUMENTS

| EP | 2384771 A1 | 11/2011 |
| WO | 03103387 A2 | 12/2003 |

OTHER PUBLICATIONS

PCT/US2013/051782 International Search Report dated Feb. 27, 2014.

*Primary Examiner* — Joseph M Pelham

(57) ABSTRACT

A method of emitting a volatile material includes the step of programming a volatile material dispenser to include at least two intensity levels, wherein upon initiation of each of the intensity levels for an operating cycle, a resistor is operated at a first percentage of its power rating for a first period of time. Upon selection of a first of the at least two intensity levels and after the first period of time, the resistor is operated at a second percentage of its power rating for a remainder of an operating cycle. Upon selection of a second of the at least two intensity levels and after the first period of time, the resistor is operated at the second percentage of its power rating for a second period of time and, after the second period of time, operating the resistor at a third percentage of its power rating for a remainder of an operating cycle.

9 Claims, 23 Drawing Sheets

(56) References Cited

U.S. PATENT DOCUMENTS

| | | |
|---|---|---|
| 6,487,367 B2 | 11/2002 | Vieira |
| 6,501,906 B2 | 12/2002 | Vieira |
| 6,563,091 B2 | 5/2003 | Vieira |
| 6,594,445 B2 | 7/2003 | Basaganas Millan |
| 6,782,194 B2 | 8/2004 | Schneiderbauer |
| 6,859,615 B2 | 2/2005 | Yip et al. |
| 6,909,840 B2 | 6/2005 | Harwig et al. |
| 7,014,818 B2 | 3/2006 | Rymer |
| 7,167,641 B2 | 1/2007 | Tam et al. |
| 7,519,279 B2 | 4/2009 | Zobele |
| 7,643,734 B2 * | 1/2010 | Wefler .......................... 392/395 |
| 7,687,744 B2 * | 3/2010 | Walter et al. .................. 219/505 |
| 7,932,482 B2 * | 4/2011 | Norwood et al. ............. 219/506 |
| 7,962,017 B2 | 6/2011 | Viera |
| 2004/0033067 A1 * | 2/2004 | He et al. ........................ 392/395 |
| 2004/0071456 A1 | 4/2004 | Levine et al. |
| 2004/0105669 A1 * | 6/2004 | He et al. ........................ 392/395 |
| 2005/0069307 A1 * | 3/2005 | He et al. ........................ 392/395 |
| 2006/0237439 A1 * | 10/2006 | Norwood et al. ............. 219/506 |
| 2011/0132992 A1 * | 6/2011 | Hoppe et al. ...................... 239/6 |

\* cited by examiner

VOLATILE MATERIAL DISPENSER AND METHOD OF EMITTING A VOLATILE MATERIAL

BACKGROUND

1. Field of the Disclosure

The present invention relates generally to volatile material dispensers, and more particular, to volatile material dispensers utilizing a heater to emit a volatile material therefrom.

2. Description of the Background

Various volatile material dispensers are known in the prior art and generally include a housing with a refill inserted therein. The refill generally includes a container for holding a volatile material therein. In some dispensers, the volatile material is passively emitted therefrom. In other dispensers, a diffusion element is utilized to facilitate the dispensing of the volatile material. Examples of diffusion elements include heaters, piezoelectric elements, fans, aerosol actuators, and the like. Regardless of the manner in which the volatile material is emitted, once the volatile material has been expended from the refill, the refill is removed by a user and replaced with a new refill.

One type of volatile material dispenser, referred to herein as a plug-in dispenser, includes a housing and a heater disposed within the housing. A refill for use with a plug-in dispenser generally includes a container with a volatile material therein and a wick in contact with the volatile material and extending out of the refill. Upon insertion of the refill into the dispenser, at least a portion of the wick is disposed adjacent the heater such that volatile material that moves through the wick is volatilized by the heater. The volatile material dispenser typically includes a plug assembly having electrical prongs extending outwardly from the housing. The electrical prongs are inserted into a standard electrical outlet and thereafter supply electrical energy to the volatile material dispenser.

SUMMARY

According to a first aspect of the present invention, a method of emitting a volatile material from a volatile material dispenser includes the step of providing a volatile material dispenser having a housing and a heater disposed within the housing, wherein the heater includes a resistor having a particular power rating. The method further includes the step of programming the volatile material dispenser to include at least two intensity levels, wherein upon initiation of each of the intensity levels for an operating cycle, the resistor is operated at a first percentage of its power rating for a first period of time. Upon selection of a first of the at least two intensity levels and after the first period of time, the resistor is operated at a second percentage of its power rating for a remainder of an operating cycle. Upon selection of a second of the at least two intensity levels and after the first period of time, the resistor is operated at the second percentage of its power rating for a second period of time and, after the second period of time, the resistor is operated at a third percentage of its power rating for a remainder of an operating cycle. The first percentage is greater than the second percentage and the second percentage is greater than the third percentage.

According to another aspect of the present invention, a refill having a volatile material contained therein includes a container having a body and a cylindrical neck forming an opening. The refill further includes a volatile material disposed within the body of the container and a wick in contact with the volatile material and extending out of the container through the opening. A wick holder for retaining the wick within the cylindrical neck of the container includes an outer surface in contact with the cylindrical neck and an inner surface having a plurality of fins extending outwardly from the inner surface for centering and retaining the wick within the wick holder.

According to still another aspect of the present invention, a volatile material dispenser includes a housing having a channel adapted for insertion of a wick extending from a refill having a volatile material. The dispenser further includes a heater disposed within the housing, the heater including a positive temperature coefficient element. A metallic ring is in conductive contact with the positive temperature coefficient element, wherein the metallic ring surrounds the channel and the wick when a refill is disposed within the dispenser. Heat from the positive temperature coefficient element travels through the metallic ring to form a ring of heat that evenly heats a circumference of the wick.

According to yet a further aspect of the present invention, a volatile material dispenser includes a housing having a channel adapted for insertion of a wick extending from a refill having a volatile material. A heater block is disposed within the housing and includes a channel, a first resistor disposed on a first side of the channel, and a second resistor disposed on a second side of the channel. Each of the resistors extends between first and second opposite sides of the heating block. First sets of leads extend from the first and second resistors, out of the first side of the heating block, and leading to a source of power. Second sets of leads extend from the first and second resistors, out of the second side of the heating block, and are spliced outside the heating block.

BRIEF DESCRIPTION OF THE DRAWINGS

Other aspects and advantages of the present invention will become apparent upon consideration of the following detailed description, wherein similar structures have like or similar reference numerals.

DETAILED DESCRIPTION

The present invention is directed to volatile material dispensers. While the present invention may be embodied in many different forms, several specific embodiments are discussed herein with the understanding that the present invention is to be considered only as an exemplification of the principles of the invention, and it is not intended to limit the invention to the embodiments illustrated.

Figure 1:
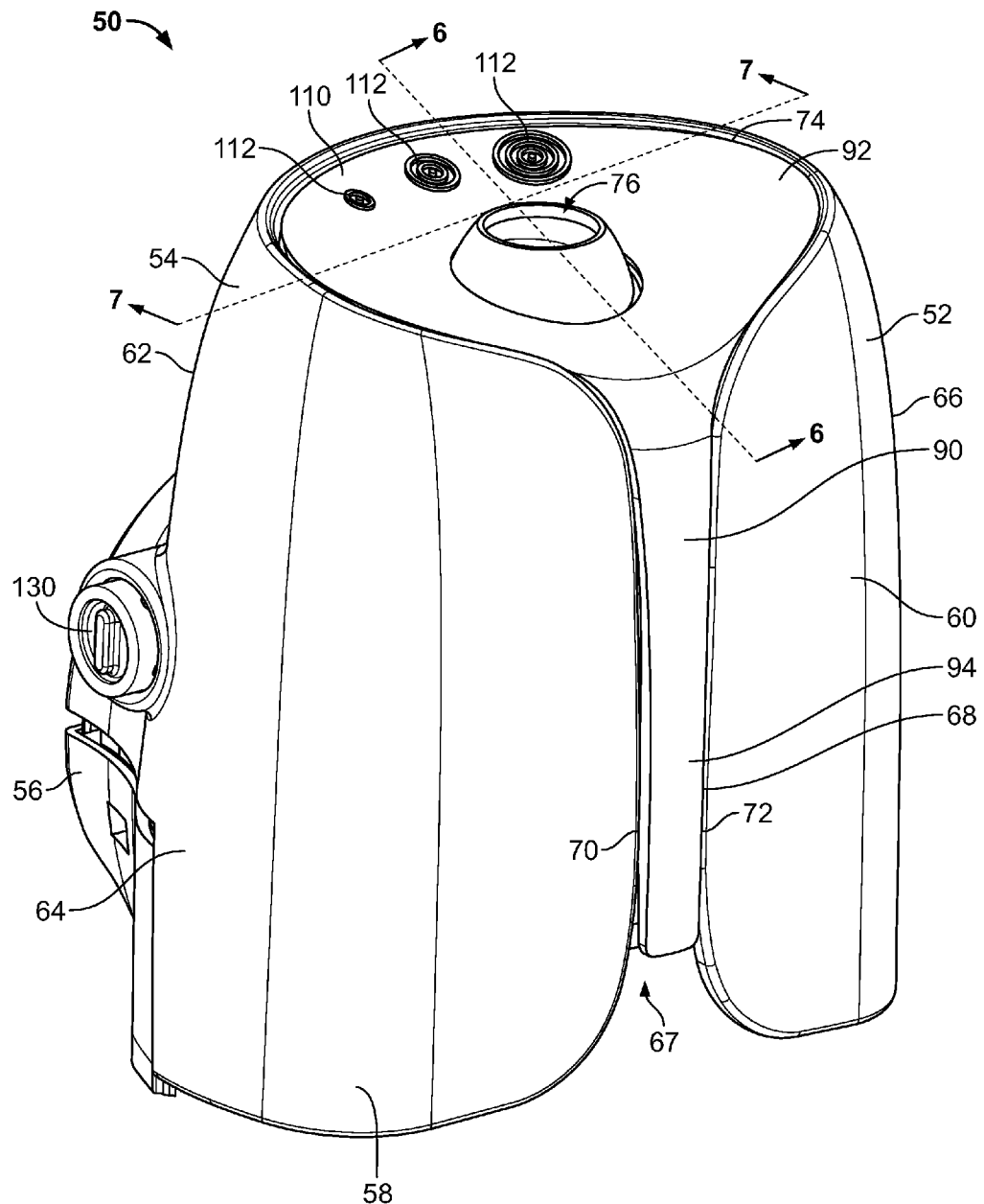
FIG. 1 is an isometric view depicting a first side, a front, and a top of a first embodiment of a volatile material dispenser according to the present invention.
Figure 2:
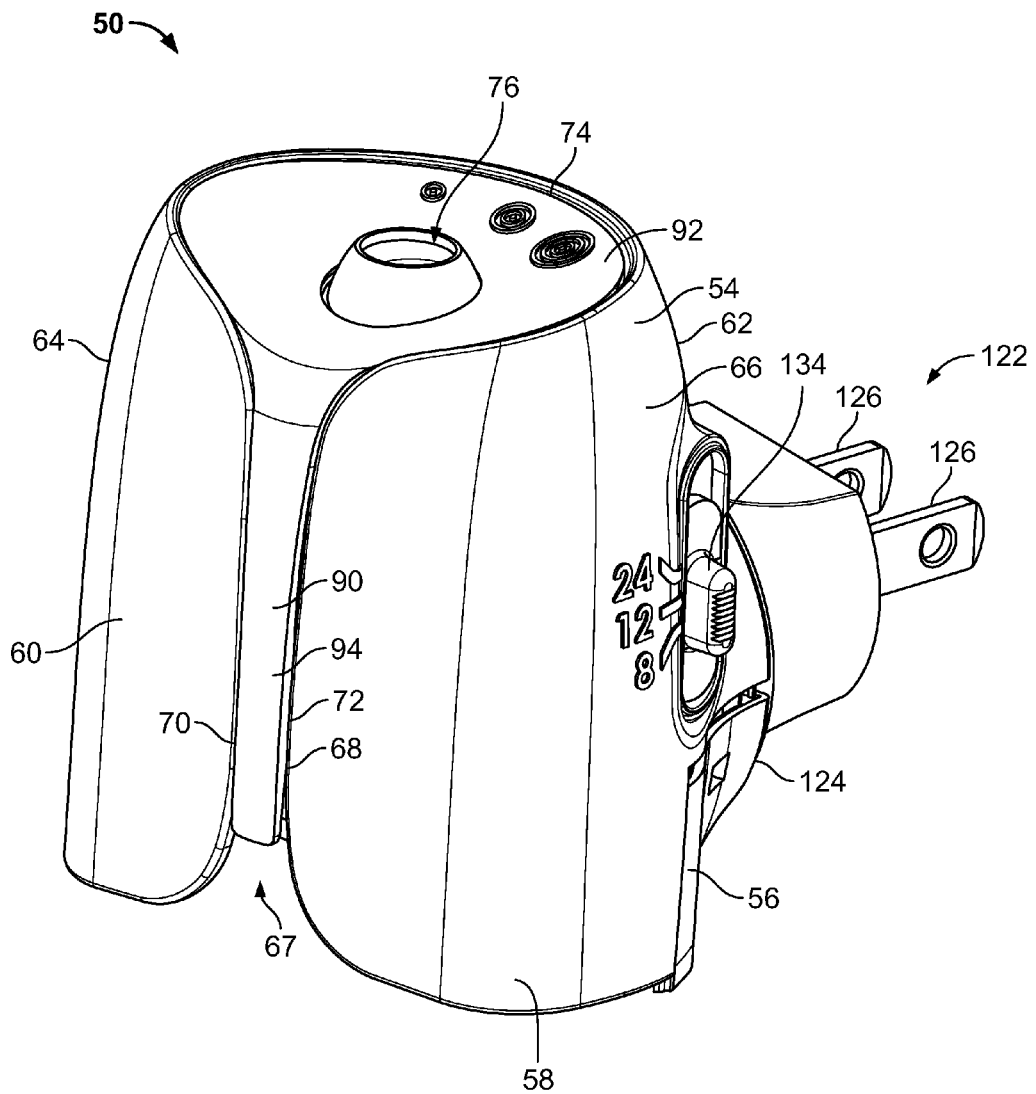
FIG. 2 is an isometric view depicting a second side, the front, and the top of the volatile material dispenser of FIG. 1.
Figure 18A:
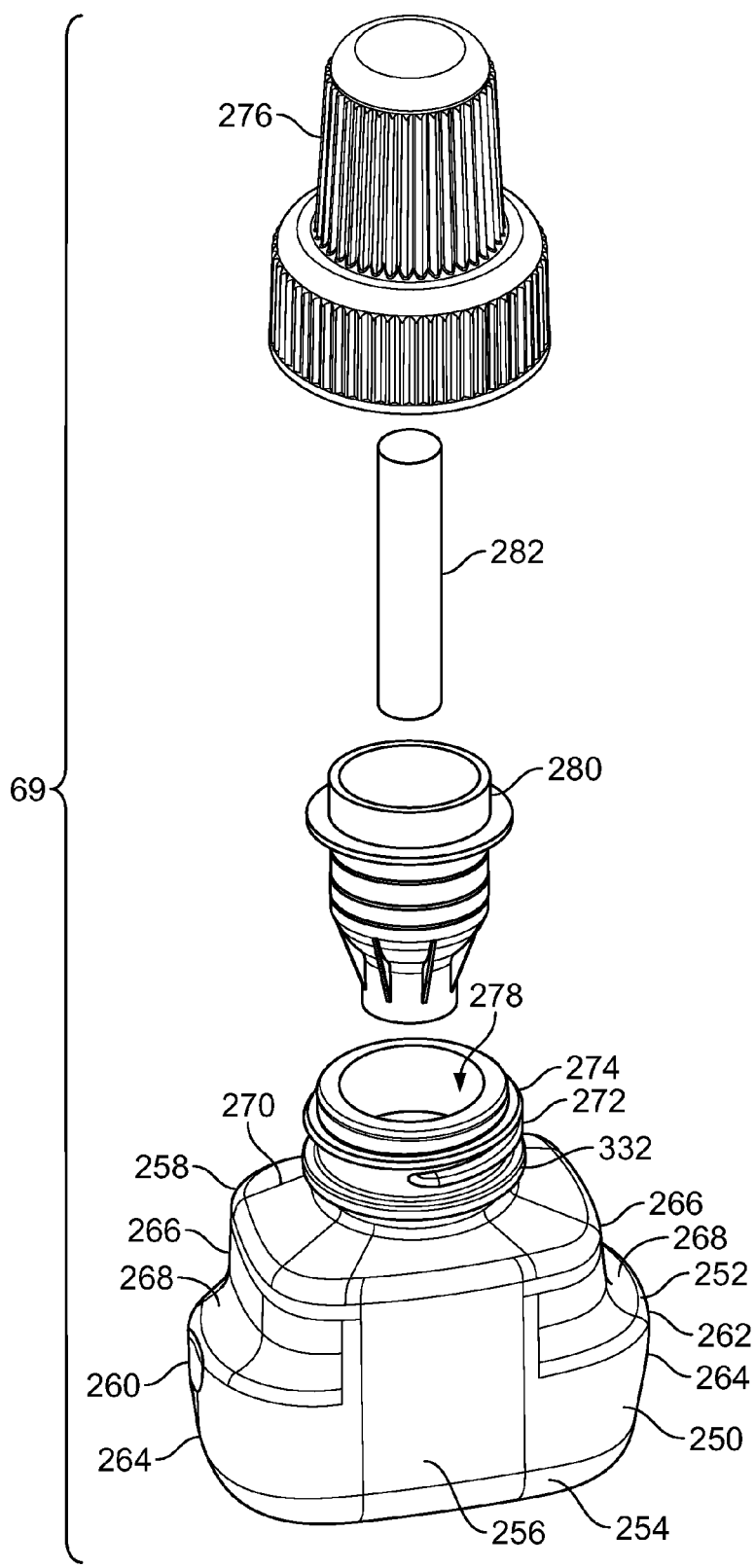
FIGS. 18A-18C are top isometric views of small, medium, and large-sized refills, respectively.
Figure 18B:
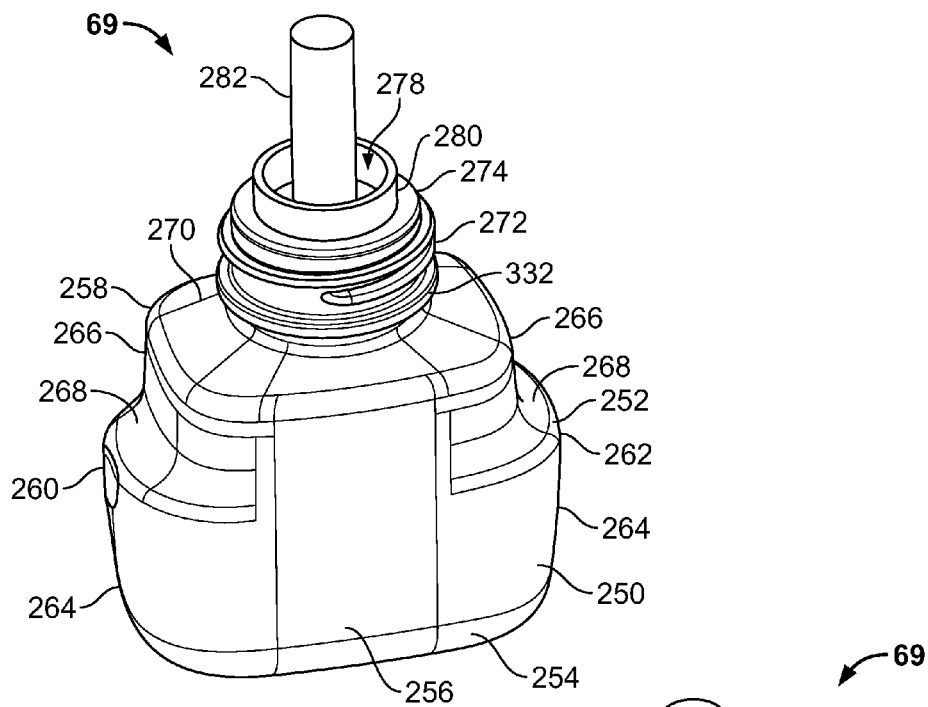
Figure 18C:
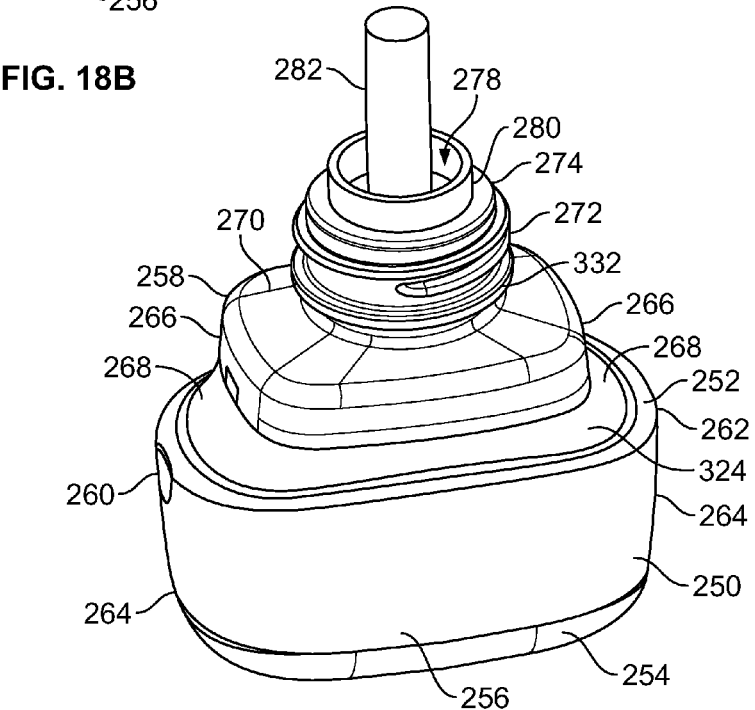

Referring to the drawings, FIGS. 1-10 depict a first embodiment of a volatile material dispenser 50. The dispenser 50 generally includes housing 52 comprised of top and bottom portions 54, 56 that are joined to form the housing 52. The housing 52 could optionally be made of any number of pieces. As best seen in FIGS. 1 and 2, the housing 52 generally includes a discontinuous oval-shaped wall 58 with a front surface 60, a rear surface 62, and first and second opposing curved side surfaces 64, 66. A bottom of the wall 58 is not enclosed, thereby forming a cavity 67 for insertion of a refill 69, as seen in FIGS. 18A-18C. A gap 68 is formed between edges 70, 72 of the wall 58, wherein a groove is formed within the gap 68. The housing 52 further includes an inset top surface 74 connecting the front, rear, and side surfaces 60, 62, 64, 66, wherein an emission aperture 76 is formed within a central portion of the top surface 74.

Figure 5:
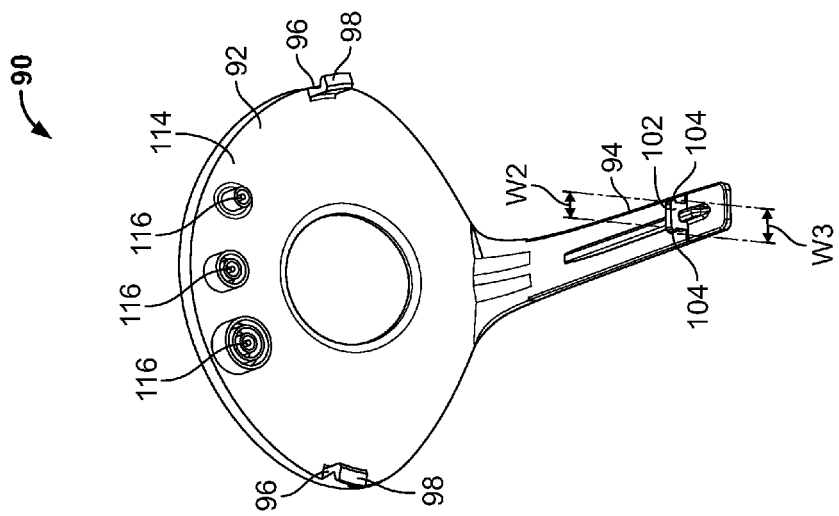
FIG. 5 is a bottom isometric view of the insert of FIG. 4.
Figure 4:
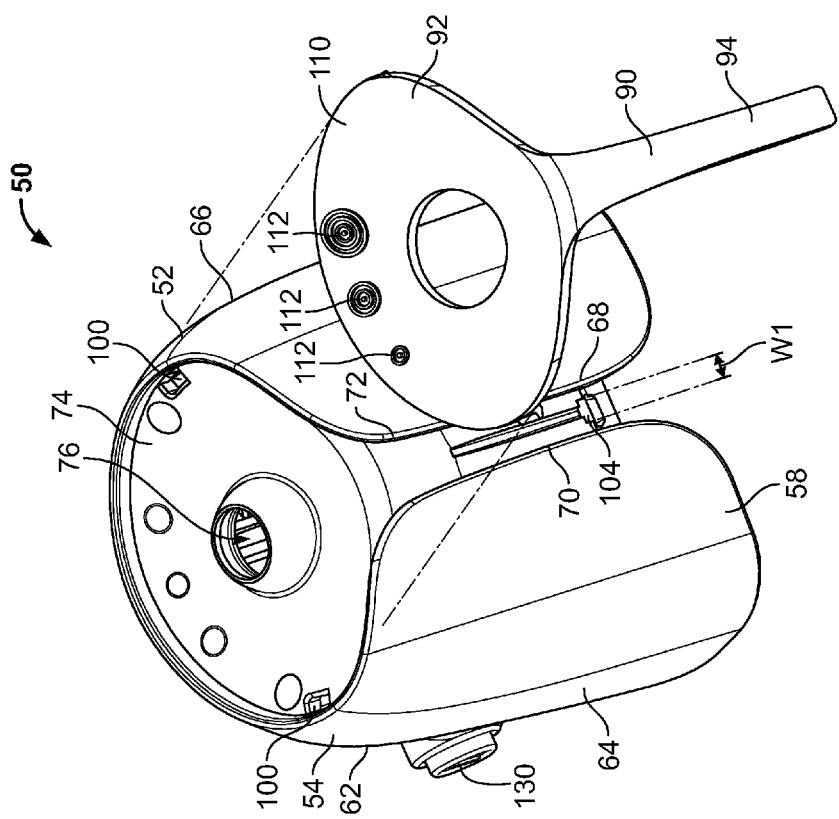
FIG. 4 is a top isometric view of the volatile material dispenser of FIG. 1 showing a insert removed therefrom.
Figure 6A:
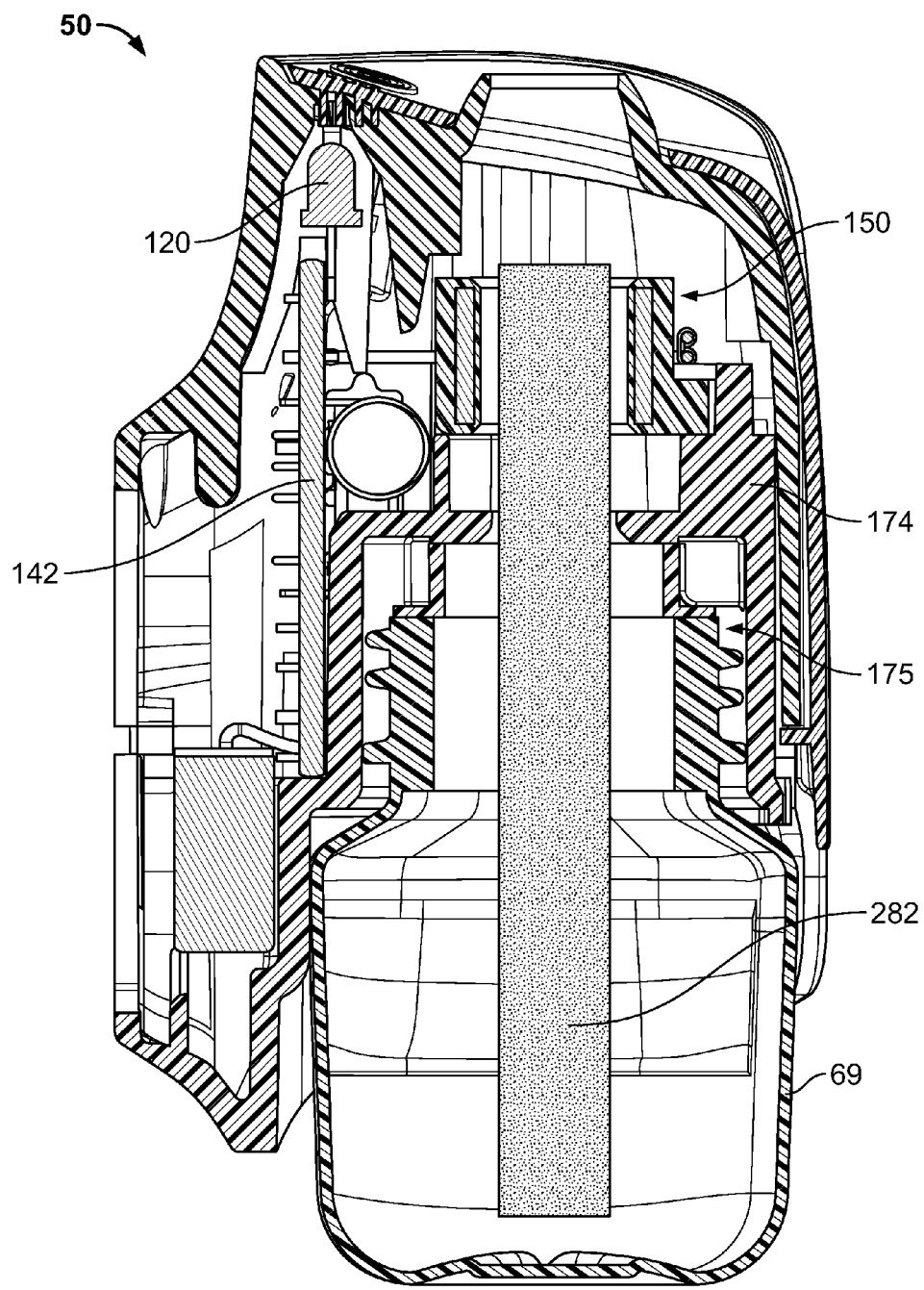
FIG. 6A is a cross-sectional view taken generally along the lines 6-6 of FIG. 1 and showing a small-sized refill disposed within the volatile material dispenser.
Figure 6B:
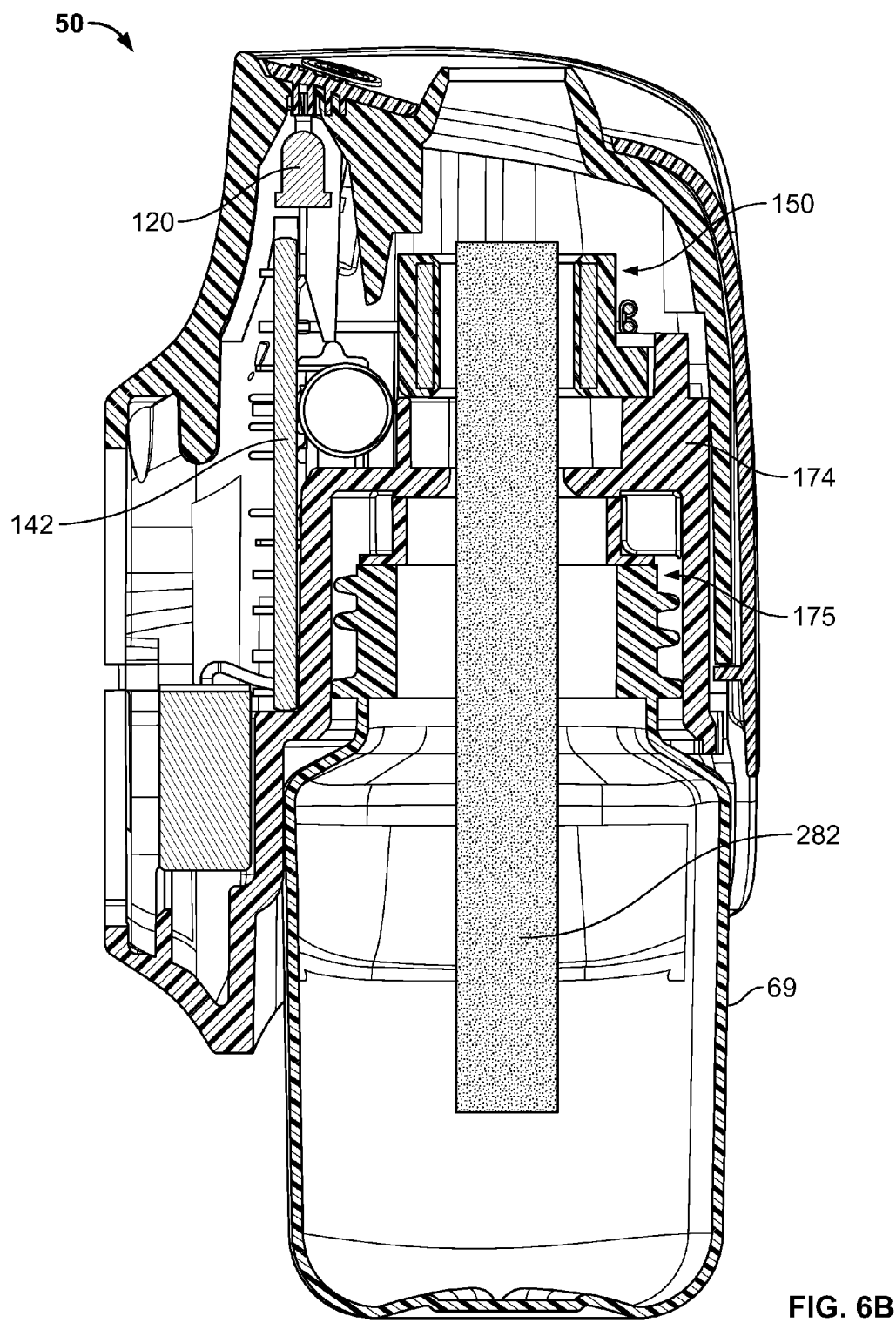
FIG. 6B is a cross-sectional view similar to that of FIG. 6A and showing a medium-sized refill disposed within the volatile material dispenser.
Figure 6C:
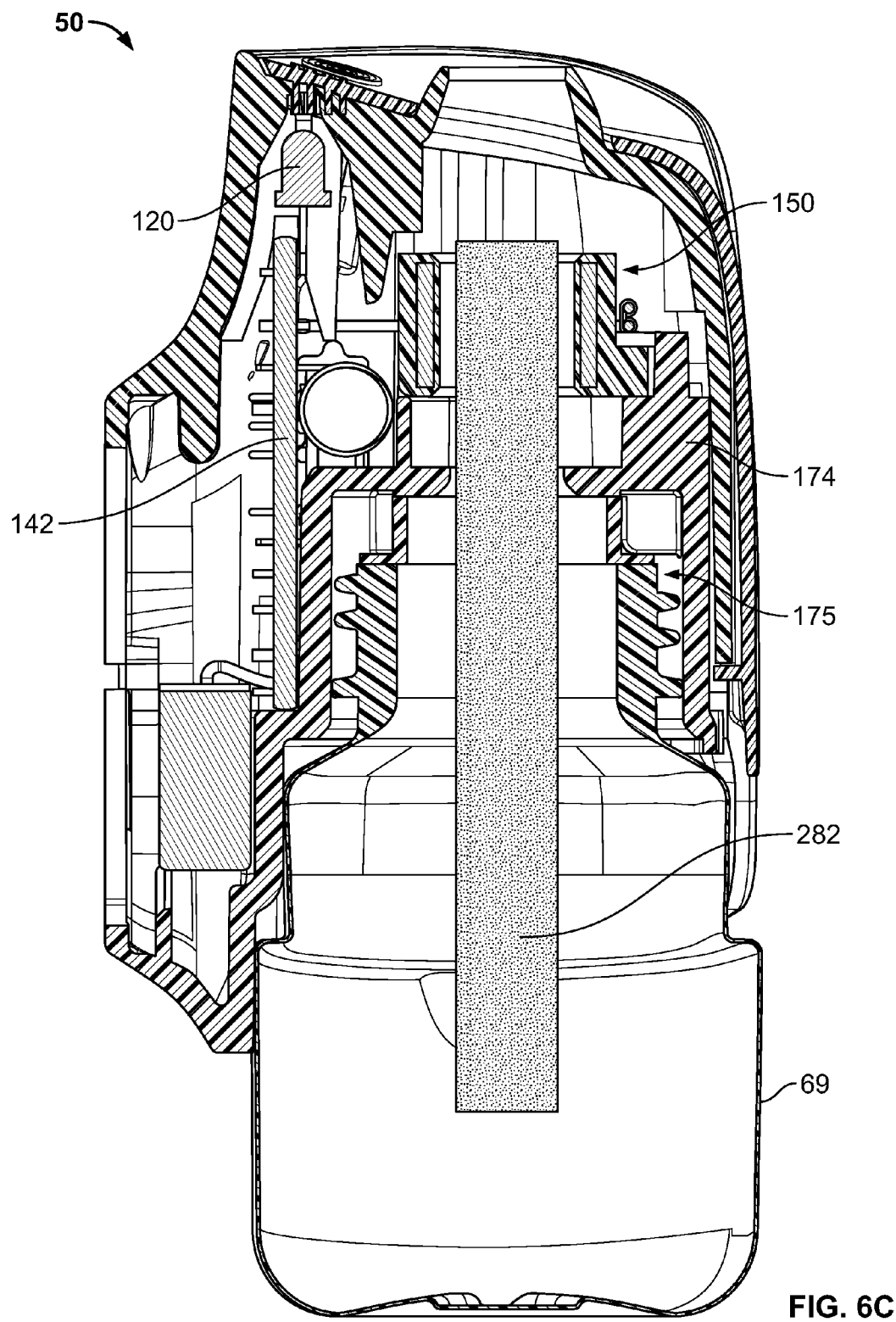
FIG. 6C is a cross-sectional view similar to that of FIG. 6A and showing a large-sized refill disposed within the volatile material dispenser.
Figure 7:
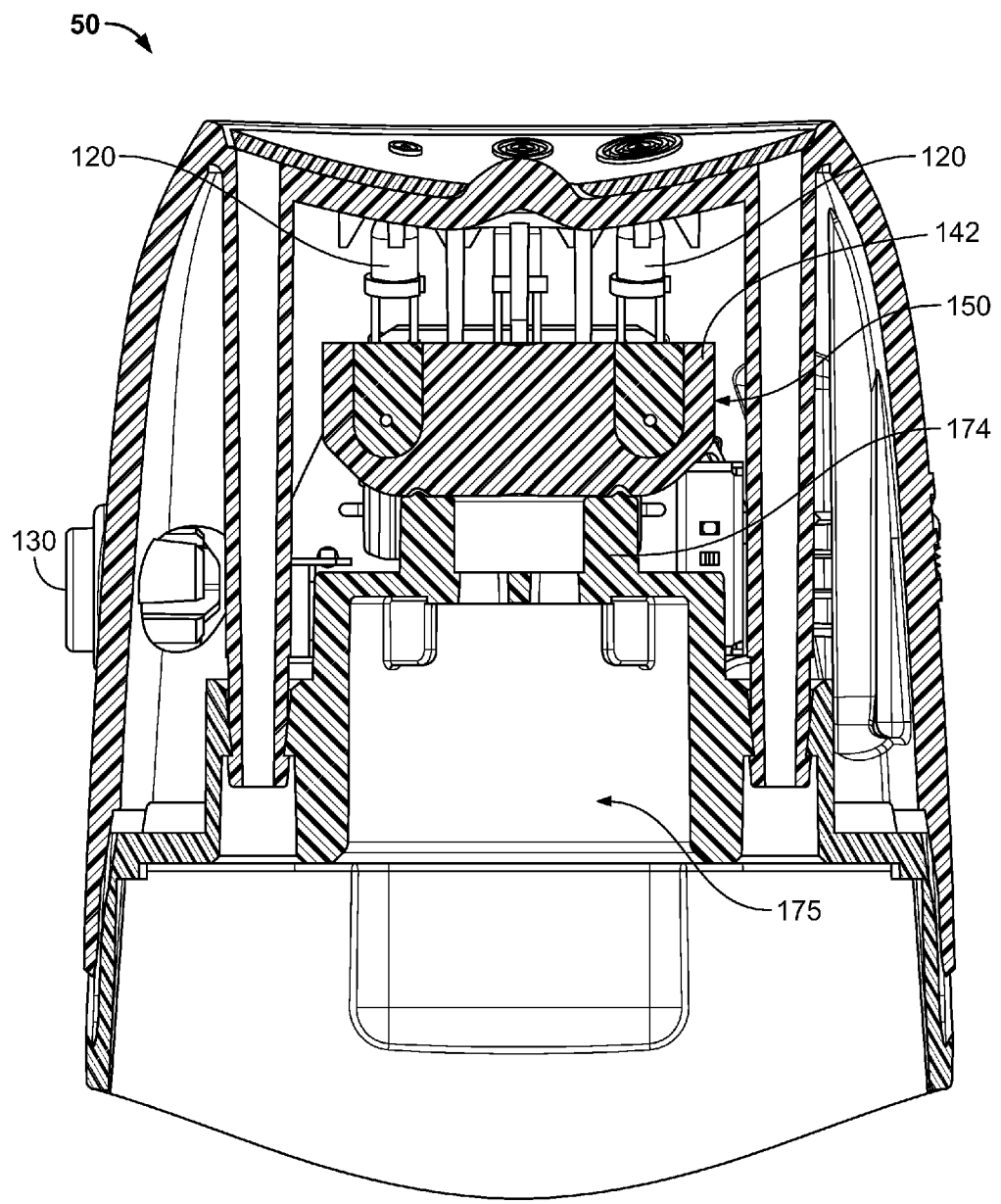
FIG. 7 is a cross-sectional view taken generally along the lines 7-7 of FIG. 1.

Referring to FIGS. 4 and 5, an insert 90 is detachably attached within the inset top surface 74 and the gap 68. In particular, the insert 90 includes a top wall 92 that curves into a side wall 94 that is generally perpendicular to the top wall 92. The top wall 92 includes first and second latches 96 with outwardly extending hooks 98 that extend into apertures 100 formed at an outer edge of the top surface 74 of the housing 52. The side wall 94 also includes a latch 102 having two outwardly extending projections 104 that engages a groove 106 disposed within the gap 68, wherein the groove 106 has a width W1 that is greater than a width W2 of a middle section 108 of the latch 102, but less than an overall width W3 of the latch 102. In this manner, the projections 104 prevent removal of the insert 90.

The insert 90 is attached to the housing 52 by inserting the middle section 108 of the latch 102 into the groove 106 and, thereafter, snapping the hooks 98 into the apertures 100. The insert 90 may be removed in an opposite manner. In particular, a user may pull upwardly on the insert 90 such that the hooks 98 are removed from the apertures 100 and thereafter, move the insert 90 downwardly such that the latch 102 is removed from the groove 106. The dispenser 50 may be provided with one or more inserts 90 and/or inserts 90 may be sold separately. In this manner, users may use no insert 90 or may attach any number of different inserts 90, depending on home décor, the day of the week, the user's emotions, or for any other reason.

Referring to FIGS. 1, 2, and 5, an outer side 110 of the top wall 92 of the insert 90 includes one or more flexible designs or indicia 112 that indicate to a user an intensity level for the dispenser 50. In particular, in one embodiment, each of the indicia 112 includes one or more concentric circles. An intensity level is indicated by the number of circles, for example, fewer circles designates a lower intensity and more circles designates a higher intensity.

As seen in FIG. 5, an inner side 114 of the top wall 92 includes one or more features 116 that project from the inner side 114 of the top wall 92 to enclose one or more LEDs 120 within the housing 52. When a particular intensity level is selected by a user, the LED 120 associated with the indicia 112 for that level is illuminated.

In a further embodiment, the top wall 92 adjacent the indicia 112 is thinned so that light projected from the LEDs 120 may be visible through the thinned areas. In such an embodiment, the features 116 may or may not be present.

Referring to FIG. 2, a plug assembly 122 is disposed between the top and bottom portions 54, 56 of the housing 52 at a rear portion 124 of the housing 52. The plug assembly 122 includes two electrical prongs 126 adapted for insertion into a conventional outlet. While the plug assembly 122 is shown as being a conventional plug assembly for the United States, a plug assembly adapted for use in any other country may be utilized. In addition, the plug assembly 122 may include any features known in the art, for example, the plug assembly 122 may be partially or fully rotatable.

Figure 8:
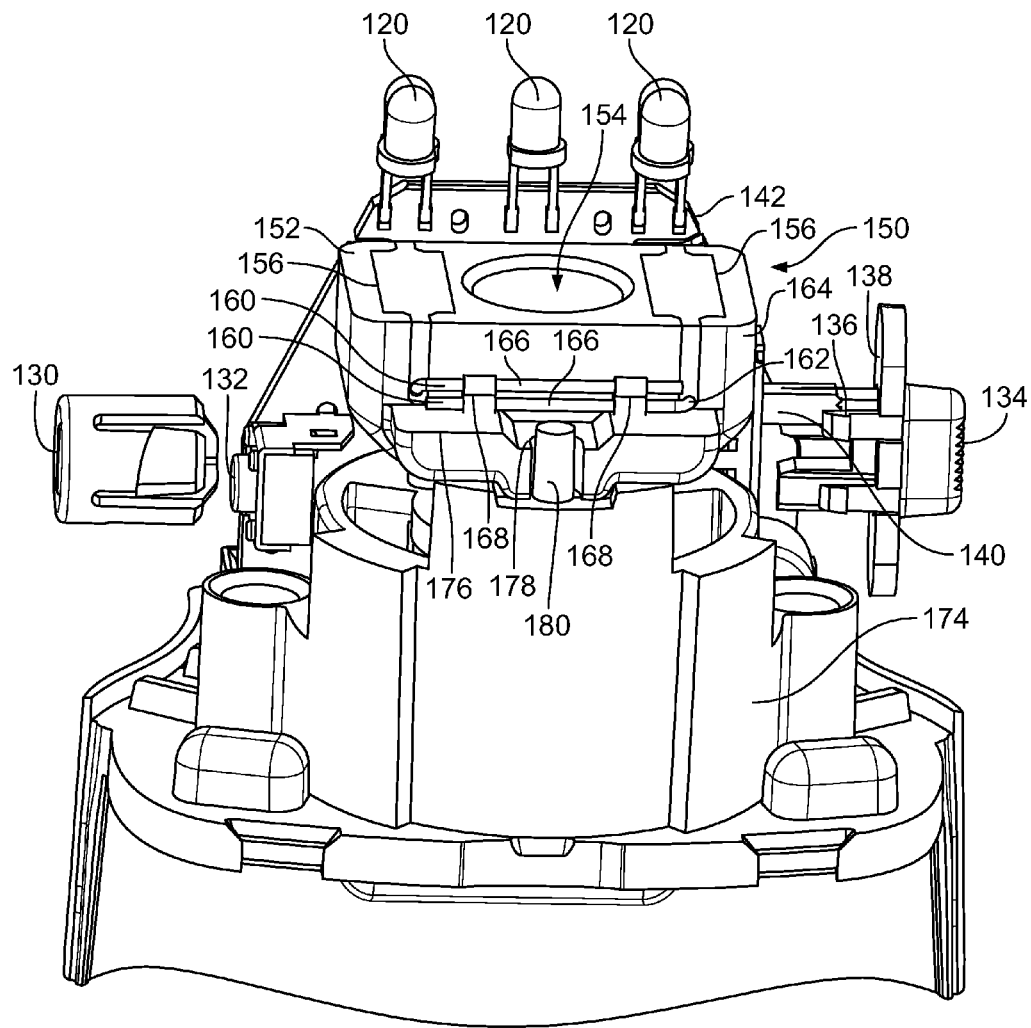
FIG. 8 is a partial exploded, top isometric view of internal components of the volatile material dispenser of FIG. 1 with front and rear housing portions removed therefrom.
Figure 9:
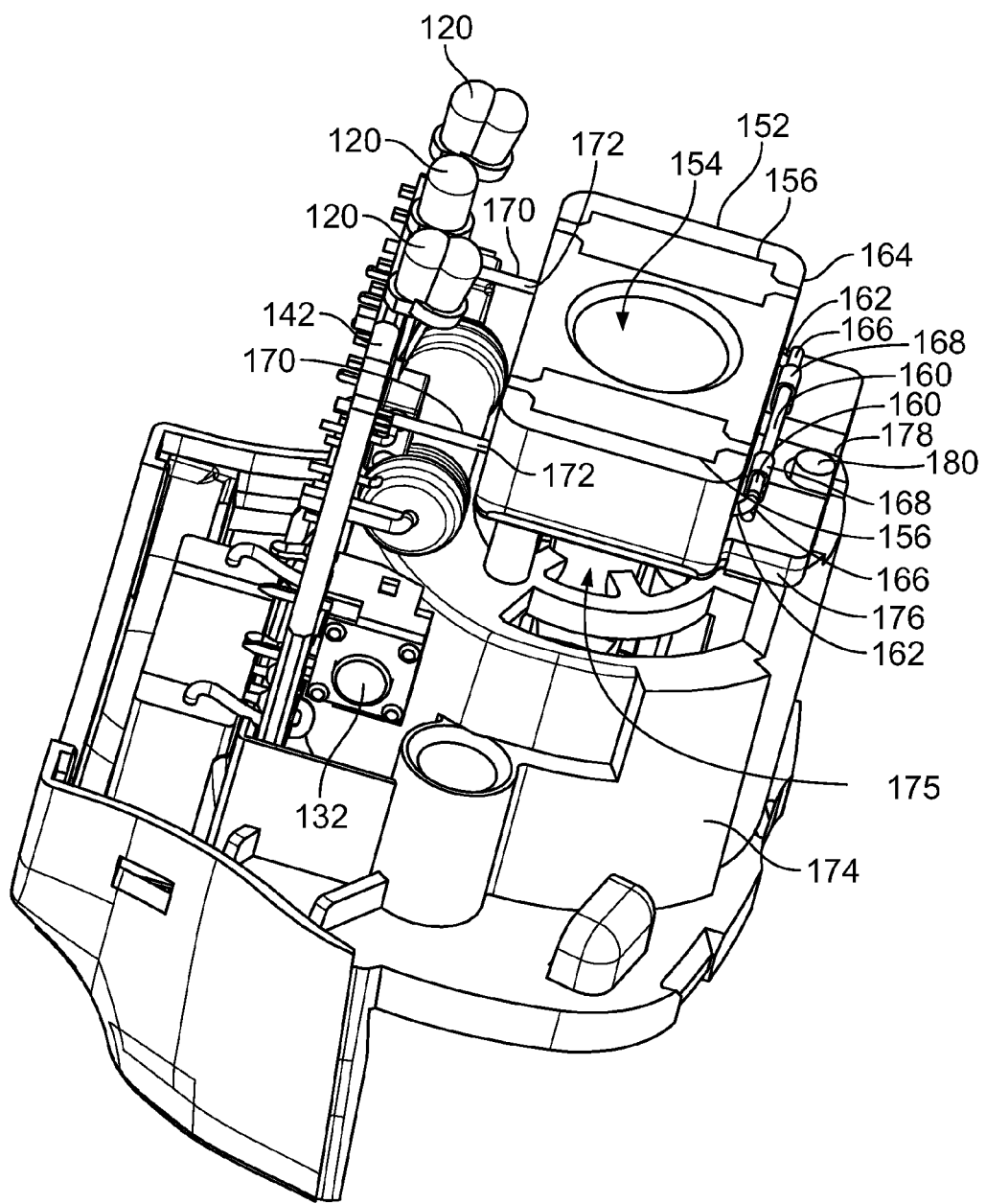
FIG. 9 is a top isometric view of the internal components of the volatile material dispenser of FIG. 1 with switches and a plug assembly further removed from FIG. 8.
Figure 10:
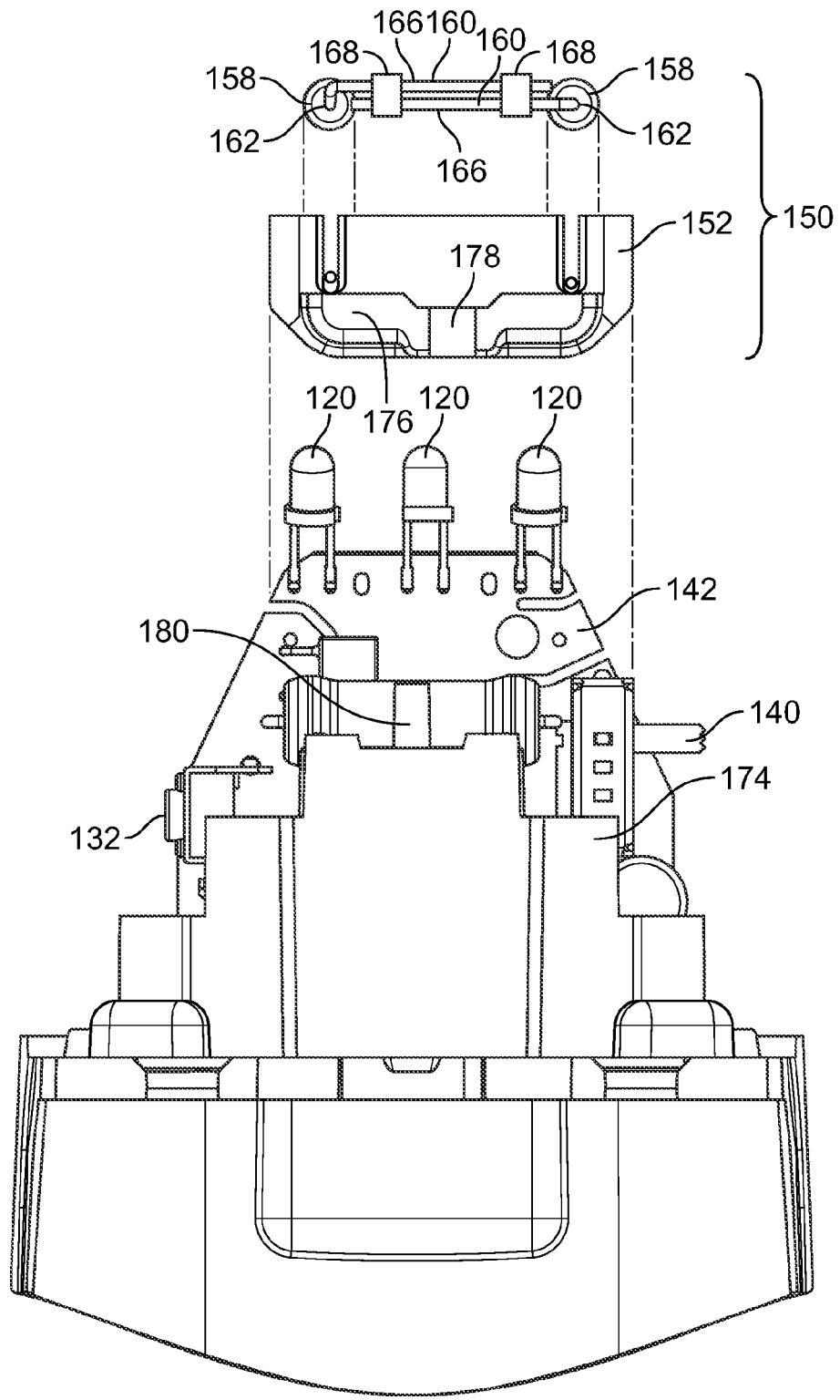
FIG. 10 is an exploded view of a heater assembly of the volatile material dispenser of FIG. 1.

A button 130 extends outwardly from the first side surface 64, as seen in FIG. 1. The button 130 is adapted to actuate a switch 132 (as seen in FIGS. 8-10) within the housing 52 and connected to a circuit board 142 (see FIGS. 6A-10) to set an intensity level of the dispenser 50. In particular, the button 130 may be pressed once for low, twice for medium, three times for high, four times for off, five times for low, and so on. As seen in FIG. 2, a slide switch 134 extends outwardly from the second side surface 66 of the housing 52 to control a mode of the dispenser 50. One or more arms 136 extend from a rear surface 138 of the sliding member 134 for communication with a rocker switch 140 within the housing 52 and connected to the circuit board 142. The operation of the switch 132 and the rocker switch 140 will be discussed in greater detail hereinafter.

A first embodiment of a heater assembly 150 for use within the dispenser 50 is best seen in FIGS. 8-10. The heater assembly 150 includes a generally rectangular heating block 152 having a central cylindrical channel 154 and cavities 156 disposed on opposite sides of the channel 154. Resistors 158 have a power rating of about 2 watts each, although resistors 158 with different power ratings may be used. The resistors 158 are disposed within the cavities 156 and the resistors 158 are potted in a ceramic or other conductive material to retain the resistors 158 within the cavities 156 and conduct heat throughout the heating block 152.

Referring to FIG. 10, a first resistor lead 160 includes a first section 162 that extends outwardly from a first side 164 of each resistor 158 and a second section 166 that extends generally transverse to the first section 162. Each of the second sections 166 extends toward the other resistor 158. The second sections 166 of the resistor leads 160 are overlapped and spliced together at splices 166. A second resistor lead 170 extends from a second side 172 of each resistor 158 and is electrically connected to the circuit board 142, which will be discussed in greater detail hereinafter.

The heater assembly 150 is disposed atop a support 174 that is connected to or integral with the housing 52 of the dispenser 50. The support 174 has a generally cylindrical profile, but may have any other profile that provides support to the heater assembly 150. A generally cylindrical channel 175 extends through the support 174 for insertion of a wick of a refill 69, as will be discussed in detail below. The support 174 and/or heater assembly 150 may also include one or more features that attach the heater assembly 150 to the support 174 or otherwise prevent the heater assembly 150 from movement within the housing 52. In one embodiment, as seen in FIGS. 9 and 10, the heater assembly 150 includes an outwardly extending platform 176 having a U-shaped groove 178 in an edge thereof, wherein a cylindrical projection 180 extending upwardly from the support 174 sits within the groove 178 to prevent side-to-side movement of the platform 176.

The circuit board 142 is best seen in FIGS. 9 and 10. As noted above, the switch 132 and the rocker switch 140 are electrically connected to the circuit board 142. When the rocker switch 140 is in a first position, a first mode is actuated in which a cycle includes operating the dispenser 50 for 8 hours and turning the dispenser 50 off for 16 hours. Similarly, when the rocker switch 140 is disposed in a second position, a second mode is actuated in which a cycle includes operating the dispenser 50 for 12 hours and turning the dispenser 50 off for 12 hours. Once a cycle of 8 hours on and 16 hours off or 12 hours on and 12 hours off is completed, the dispenser 50 automatically continues with a further cycle. This cycling continues until power to the dispenser 50 is interrupted. While two modes are disclosed, any number of modes may be utilized.

The button 130, as noted above, is pressed by a user to actuate the switch 132 and change the intensity at which the volatile material in the refill 69 is emitted. In particular, upon a first depression of the button 130, the dispenser 50 is set at a first, high intensity level. Similarly, when the switch 132 is actuated a second time, the dispenser 50 is set at a second, medium intensity level and upon a third actuation, the dispenser 50 is set at a third, low intensity level. As one skilled in the art would understand, the number of actuations corresponding to the various intensity levels may be modified without departing from the spirit of the present invention.

The first intensity level is a high level. Upon initiation of each of the first, second, and third intensity levels, the resistors 158 are operated at 99% of their power rating for a first period of time preferably between about 5 minutes and about 30 minutes, more preferably between about 7 minutes and about 20 minutes, and most preferably about 10 minutes to quickly increase the heat within the resistors 158. At the high/first intensity level, after the first period of time, the resistors 158 are operated at 96% of their power rating for the remainder of the on cycle. At the medium/second intensity level, after the first 10 minutes, the resistors 158 are operated at 96% of their power rating for a second period of time that is preferably between about 2 hours and about 6 hours, more preferably between about 3 hours and about 5 hours, and most preferably about 4 hours and, thereafter, are operated at 91% of their power rating for the remainder of the on cycle. At the low/third intensity level, after the first period of time, the resistors 158 are operated at 96% of their power rating for a third period of time that is preferably between about 30 minutes and about 90 minutes, more preferably between about 45 minutes and about 75 minutes, and most preferably about 1 hour and, thereafter, are operated at 87% of their power rating for the remainder of the on cycle. These algorithms are repeated for every on cycle.

As noted above, the resistors 158 are electrically connected to the circuit board 142 by the second resistor leads 170. The circuit board 142 is programmed to operate the resistors 158 in different manners per the switch 132 and the rocker switch 140, as described in detail above.

As further seen in FIGS. 9 and 10, the LEDs 120 are electrically connected to and extend upwardly from the circuit board 142. The LEDs 120 reside within the features 116 or at least adjacent the indicia 112 such that the LEDs 120 illuminate a respective indicia 112 to indicate which intensity level is being operated.

As noted above, the cavity 67 is formed by the housing for insertion of a refill 69 therein. A small-sized refill 69 is depicted in FIG. 18A and generally includes a container 250 with a volatile material therein, wherein the container is adapted to be retained within the housing 52. The container 250 includes a body 252 having a base portion 254, opposing front and rear walls 256, 258 extending upwardly from the base portion 254, and opposing side walls 260, 262 connecting the front and rear walls 256, 258 and extending upwardly from the base portion 254. The front and rear walls 256, 258 are generally planar and each of the side walls 260, 262 includes first and second generally planar wall sections 264, 266 connected by a curved section 268.

Still referring to FIG. 18A, the front, rear, and side walls 256, 258, 260, 262 at a shoulder portion 270 that leads into a neck 272. The neck 272 is generally cylindrical, has a threading 274 on an outer surface of the neck 272 for attachment of a cap 276 and/or attachment to a dispenser, and forms an opening 278. A wick holder 280 is disposed within the neck 272 for holding a wick 282.

Figure 19:
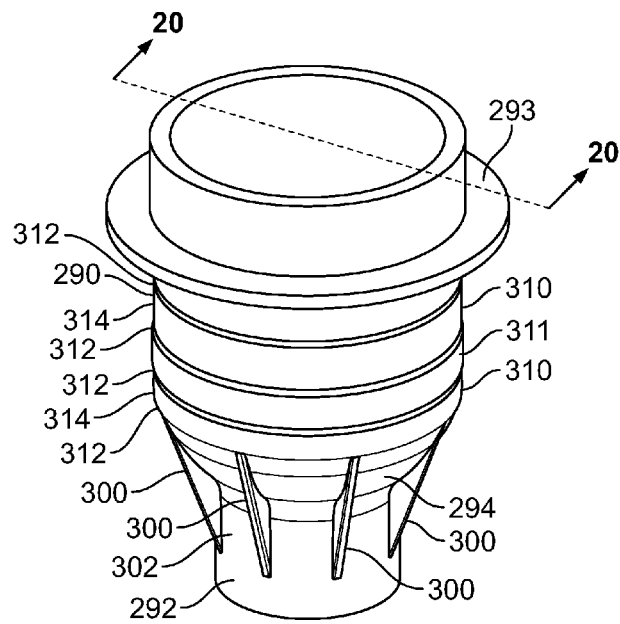
FIG. 19 is a top isometric view of a wick holder for use holding a wick within a refill, such as the small, medium, and large-sized refills of FIGS. 18A-18C.
Figure 20:
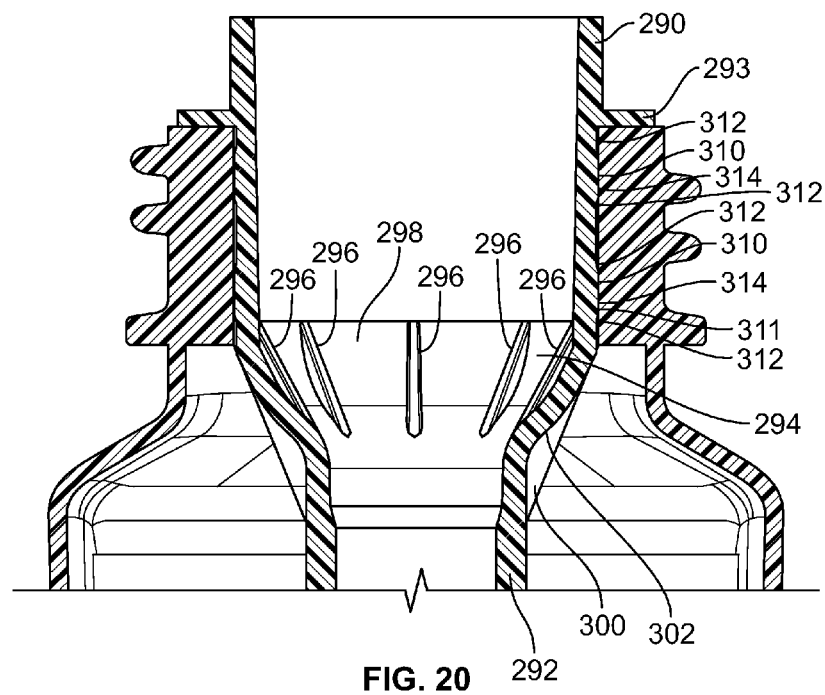
FIG. 20 is a cross-sectional view taken generally along the lines 20-20 of FIG. 19 and depicting the wick holder within an opening of a refill.

As seen in FIGS. 19 and 20, the wick holder 280 includes a first generally cylindrical wall 290 connected to a second generally cylindrical wall 292 by an angled wall 294. An annular wall 293 extends outwardly from and is generally orthogonal to the first cylindrical wall 290 to form a ledge or abutment. Referring to FIG. 20, a first plurality of angled fins 296 extend along an inner surface 298 of the curved wall 294 to give the inner surface 298 of the curved wall 294 a frustroconical shape. As seen in FIG. 19, a second plurality of angled fins 300 extend along an outer surface 302 of the wick holder 280 from a central portion of the curved wall 294 to a central portion of the second cylindrical wall 292. The second plurality of angled fins 300 forms have a profile that is generally frustroconical in shape.

Referring to FIGS. 19 and 20, one or more projections 310 extend outwardly from an outer surface 311 of the first cylindrical wall 292 of the wick holder 280. The projections 310 are formed by two angled walls 312 and a planar wall 314 connecting the angled walls 314. Upon insertion of the wick holder 280 into the neck 272 of the refill 69, the projections 310 form an interference fit with the neck 272 to provide resistance to extraction of the wick holder 280. In addition, the first plurality of angled fins 296 engage the material of the wick 282 to retain the wick 282 within the wick holder 280.

A medium-sized refill 69 is depicted in FIG. 18B and is identical to the small-sized refill 69 of FIG. 18A, except that the medium-sized refill 69 is taller. A large-sized refill 69 is depicted in FIG. 18C and is similar to the refills of FIGS. 18A and 18B, except that the front and rear walls 256, 258 also include first and second generally planar wall sections 320, 322 connected by a curved section 324, wherein the curved section 324 is connected to and continuous with the curved section 268 of the side walls 260, 262.

The volatile material disposed in the container 250 of any of the refills 69 herein may be any type of volatile material adapted to be dispensed into an environment. For example, the container 250 may include a cleaner, an insecticide, an insect repellant, an insect attractant, a disinfectant, a mold or mildew inhibitor, a fragrance, a disinfectant, an air purifier, an aromatherapy scent, an antiseptic, an odor eliminator, a positive fragrancing volatile material, an air-freshener, a deodorizer, or the like, and combinations thereof. Additives may be included in the volatile material, such as, for example, fragrances and/or preservatives.

Figure 3:
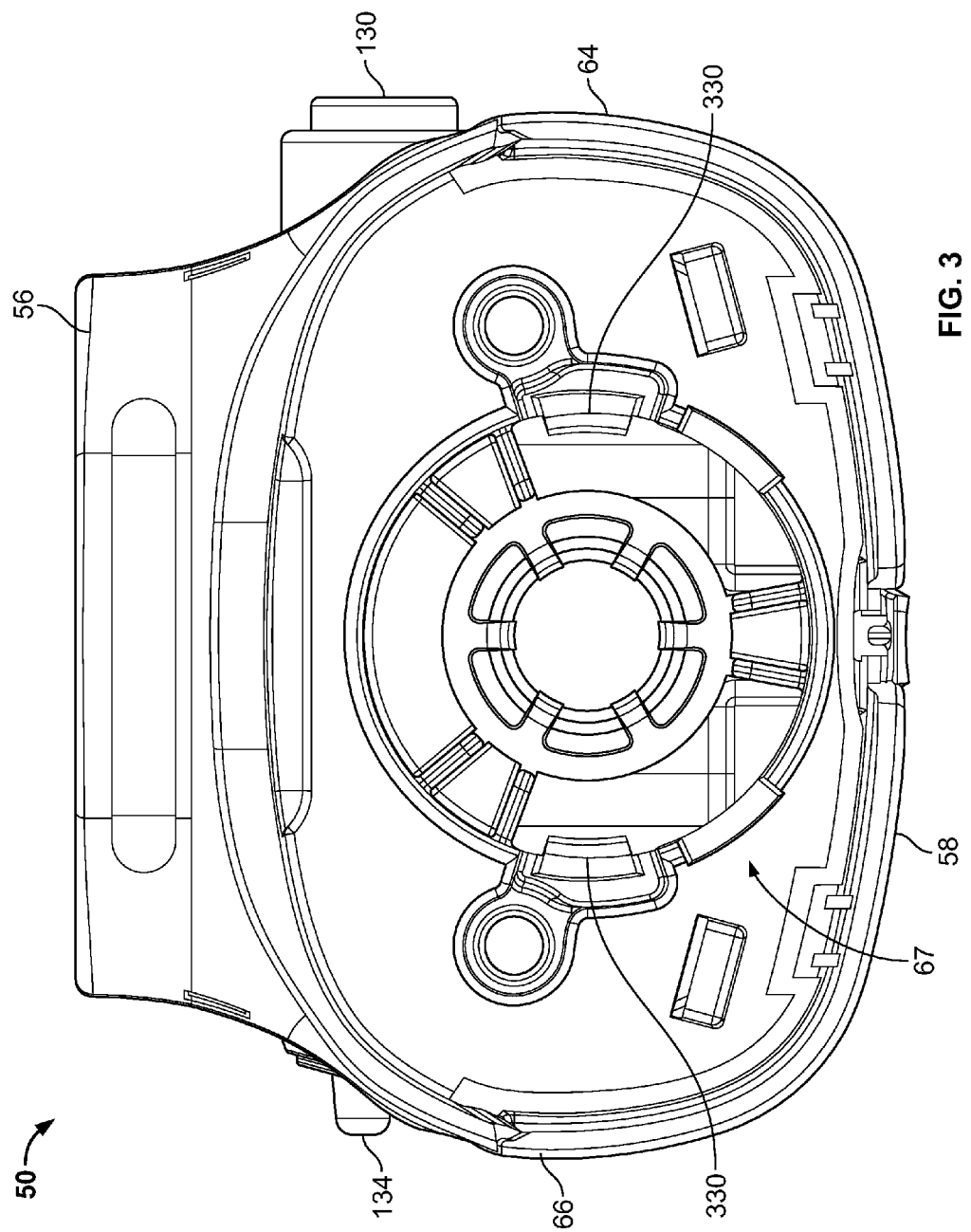
FIG. 3 is a bottom elevational view of the volatile material dispenser of FIG. 1.

As seen in FIG. 3, the dispenser 50 includes opposing resilient latches 330 extending downwardly from the support 174. As further seen in FIGS. 6A-6C, the latches 330 are capable of holding the small-sized, medium-sized, and large-sized refills 69 of FIGS. 18A-18C in two different manners. First, each refill 69 may be inserted such that the threading 274 is in contact with the latches 330 and the refill 69 can thereafter be turned to full insert the refill 69. Secondly, each refill 69 may be inserted upwardly, pushing the latches 330 outwardly, wherein the latches 330 grasp and retain the refill 69 by an annular ledge 332 disposed below the threading 274.

Figure 11:
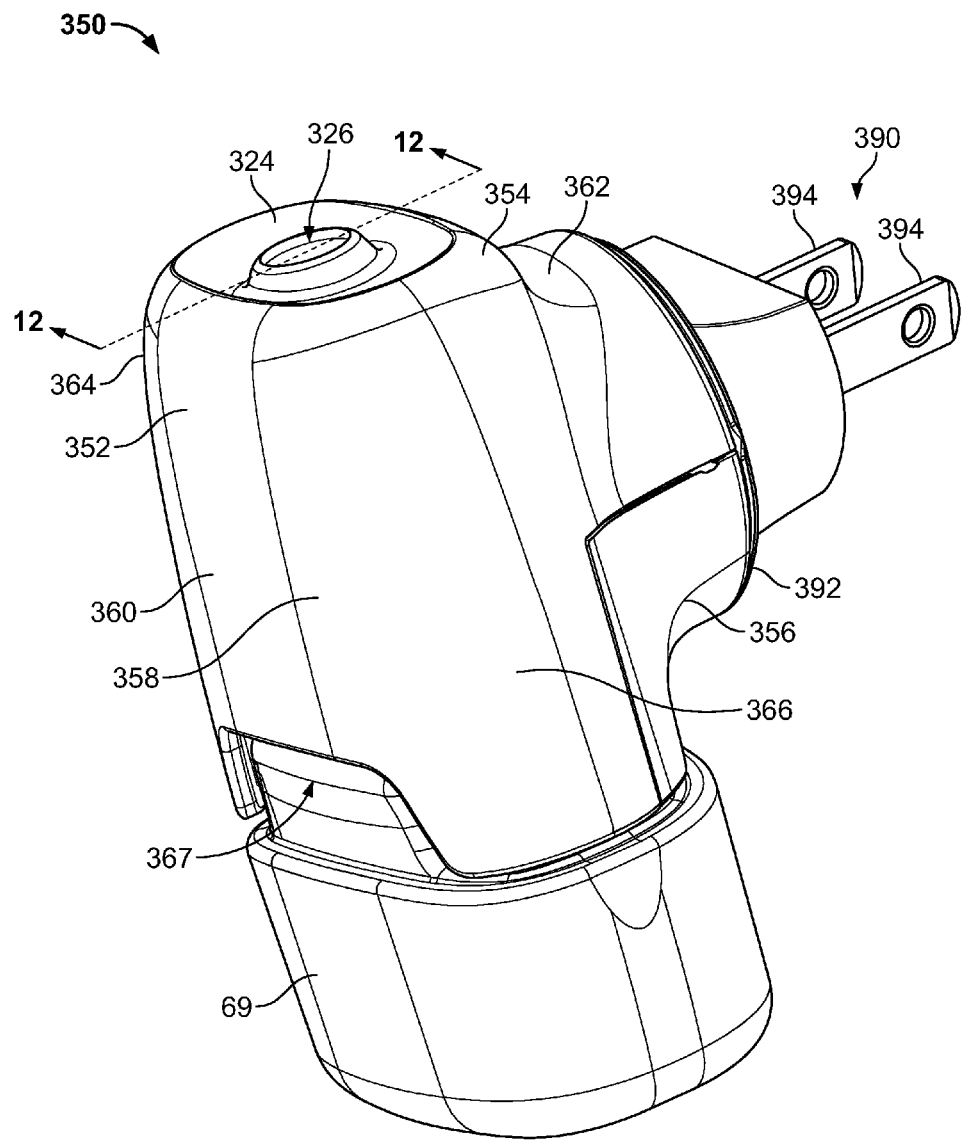
FIG. 11 is an isometric view depicting a second side, a front, and a top of a second embodiment of a volatile material dispenser.
Figure 12A:
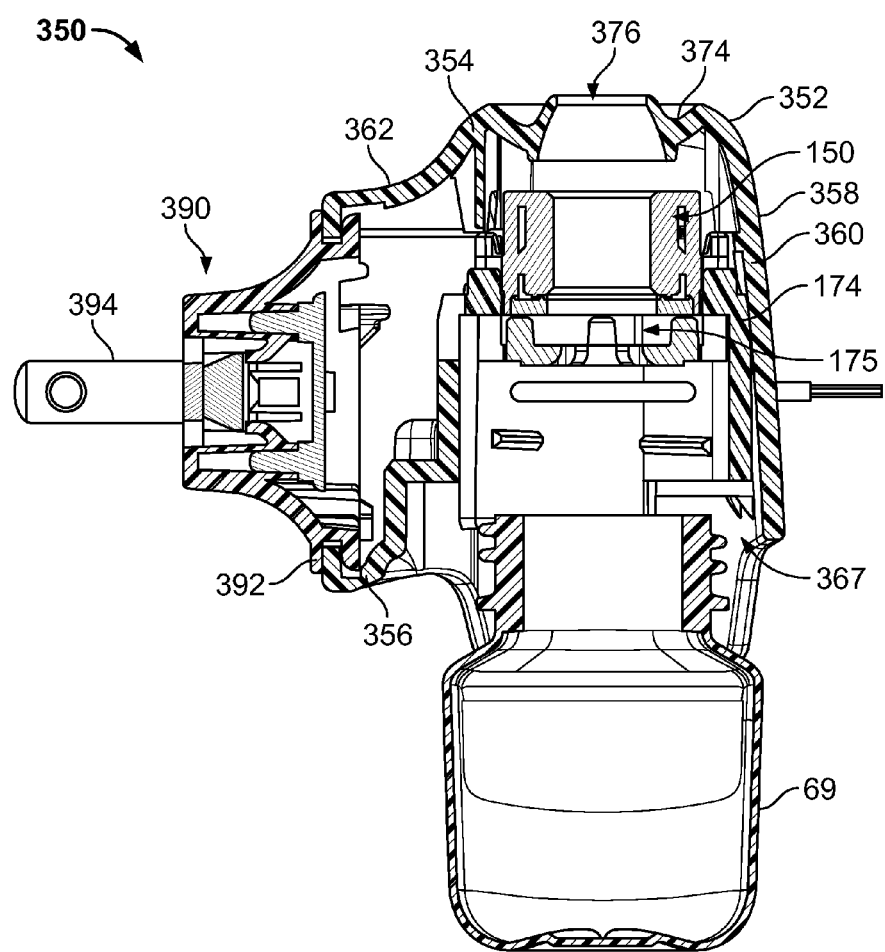
FIG. 12A is a cross-sectional view taken generally along the lines 12-12 of FIG. 11 and depicting a small-sized refill disposed within the volatile material dispenser.
Figure 12B:
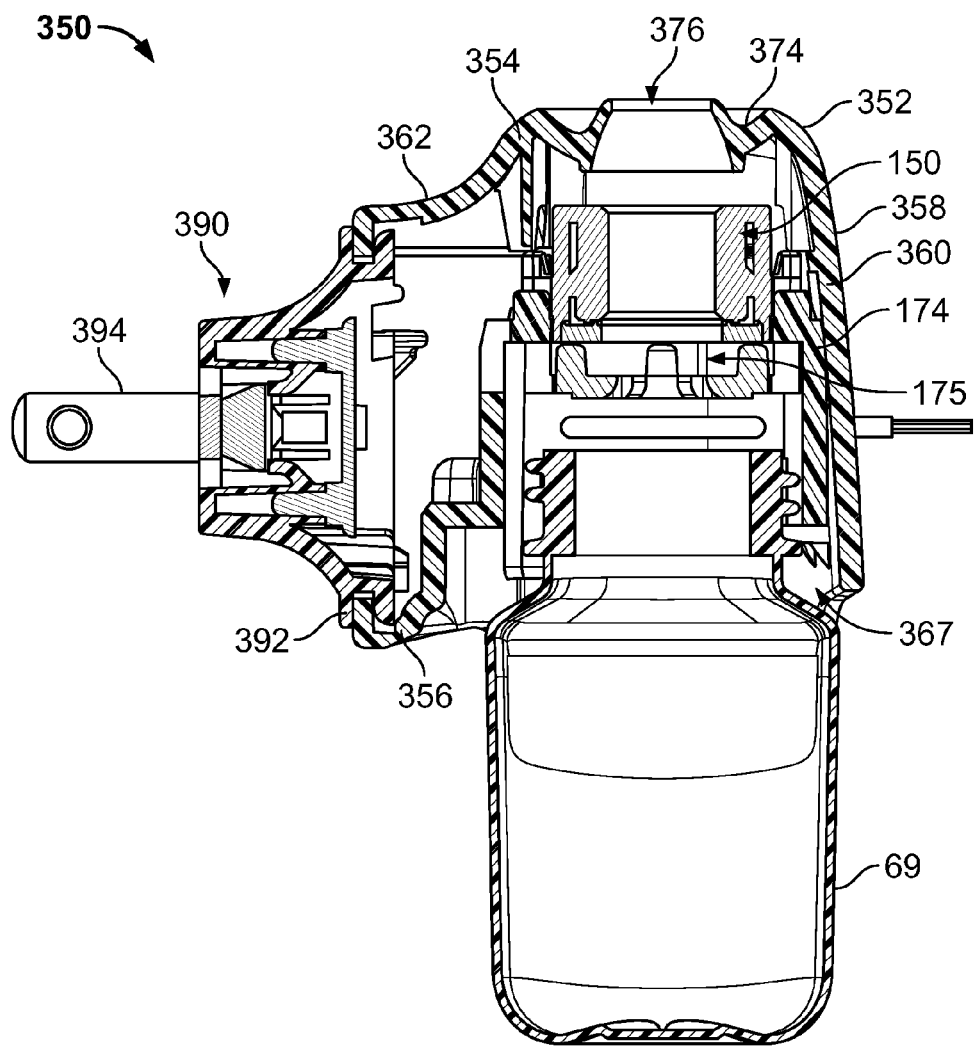
FIG. 12B is a cross-sectional view similar to that of FIG. 12A and depicting a medium-sized refill disposed within the volatile material dispenser.
Figure 12C:
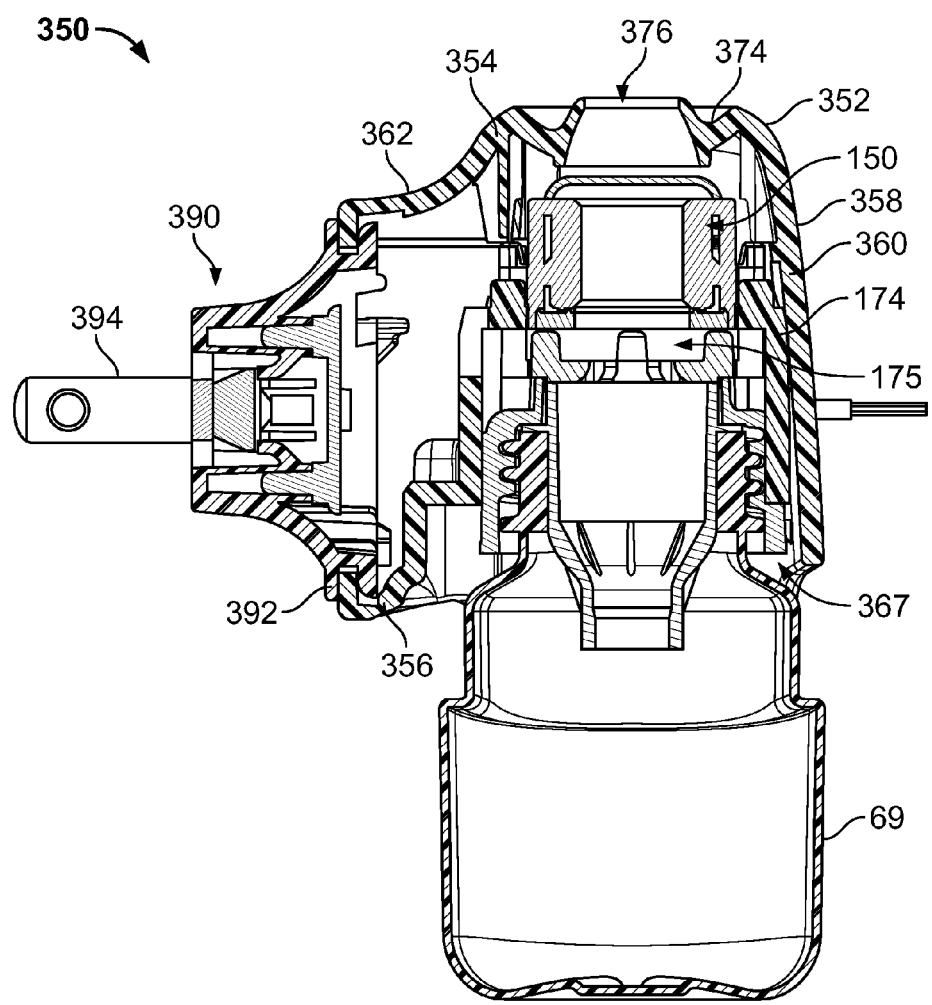
FIG. 12C is a cross-sectional view similar to that of FIG. 12A and depicting a large-sized refill disposed within the volatile material dispenser.
Figure 13:
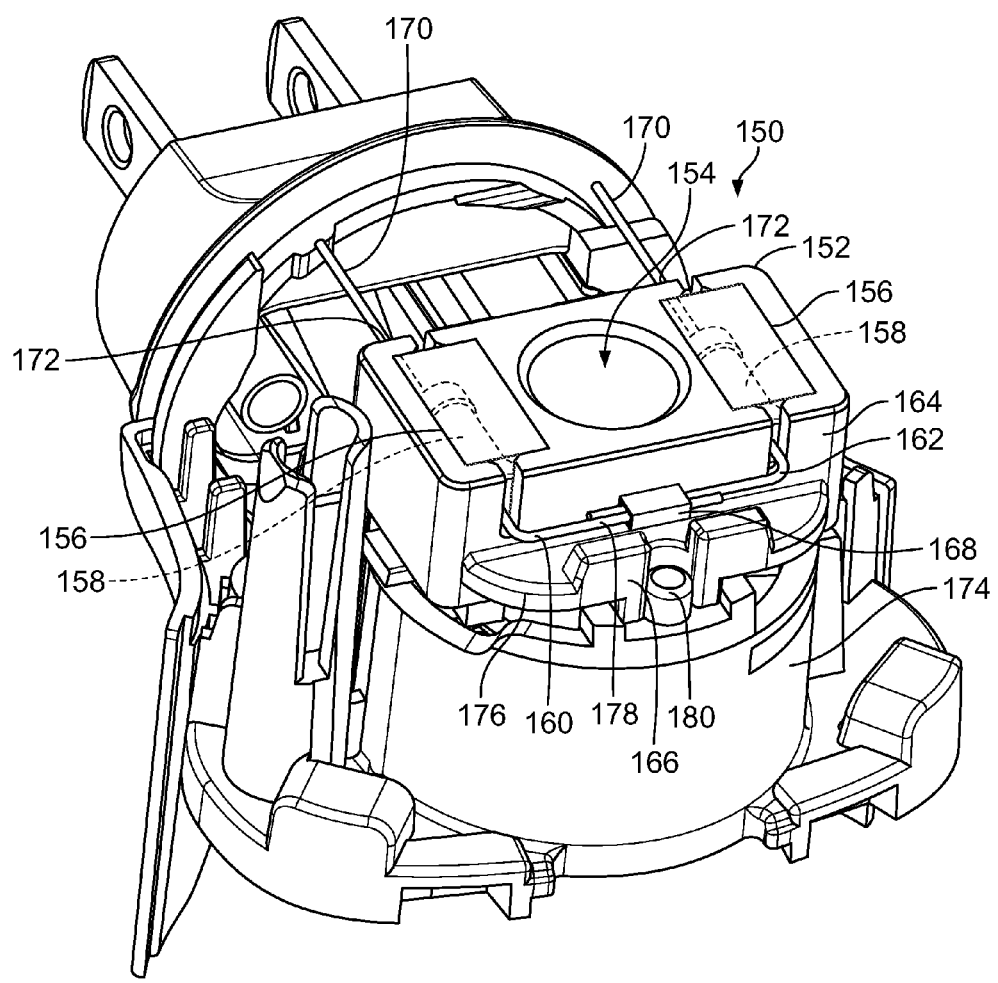
FIG. 13 is a top isometric view of internal components of the volatile material dispenser of FIG. 1 with front and rear housing portions removed therefrom and wherein a first embodiment of a heater assembly is depicted within the volatile material dispenser of FIG. 11.

A second embodiment of a volatile material dispenser 350 is depicted in FIGS. 11-13. The volatile material dispenser 350 generally includes a housing 352 comprised of top and bottom portions 354, 356 that are joined to form the housing 352. The housing 352 could optionally be made of any number of pieces. As best seen in FIG. 11, the housing 352 generally includes an oval-shaped wall 358 with a front surface 360, a rear surface 362, and first and second opposing curved side surfaces 364, 366. A bottom of the wall 358 is not enclosed, thereby forming a cavity 367 for insertion of any of the refills 69 disclosed herein, for example those shown in FIGS. 18A-18C. The housing 352 further includes an inset top surface 374 connecting the front, rear, and side surfaces 360, 362, 364, 366, wherein an emission aperture 376 is formed within a central portion of the top surface 374.

Referring to FIG. 11, a plug assembly 390 is disposed between the top and bottom portions 354, 356 of the housing 352 at a rear portion 392 of the housing 352. The plug assembly 390 includes two electrical prongs 394 adapted for insertion into a conventional outlet. While the plug assembly 390 is shown as being a conventional plug assembly for the United States, a plug assembly adapted for use in any other country may be utilized. In addition, the plug assembly 390 may include any features known in the art, for example, the plug assembly 390 may be partially or fully rotatable.

The first embodiment of a heater assembly 150 disclosed in conjunction with the first embodiment of FIGS. 1-10 is disposed within the housing 352, as seen in FIG. 13. Like components will therefore be assigned like reference numerals. In particular, the heater assembly 150 includes a generally rectangular heating block 152 having a central cylindrical channel 154 and cavities 156 disposed on opposite sides of the channel 154. Resistors 158 are disposed within the cavities 156 and the resistors 158 are potted in a ceramic or other conductive material to retain the resistors 158 within the cavities 156 and conduct heat throughout the heating block 152. The resistors 158 have power rating of about 2 watts each, although resistors 158 with different power ratings may be used.

Referring again to FIG. 13, a first resistor lead 160 includes a first section 162 that extends outwardly from a first side 164 of each resistor 158 and a second section 166 that extends generally transverse to the first section 162. Each of the second sections 166 extends toward the other resistor 158. The second sections 166 of the resistor leads 160 are overlapped and spliced together at splices 166. A second resistor lead 170 extends from a second end 172 of each resistor 158 and is electrically connected to the plug assembly 390, such that power is supplied to the resistors 158 when the dispenser 350 is plugged into an outlet.

The heater assembly 150 is disposed atop a support 174 that is connected to or integral with the housing 352 of the dispenser 350. The support 174 has a generally cylindrical profile, but may have any other profile that provides support to the heater assembly 150. A generally cylindrical channel 175 (see FIGS. 12A-12C) extends through the support 174 for insertion of a wick of a refill 69, as will be discussed in detail below. The support 174 and/or heater assembly 150 may also include one or more features that attach the heater assembly 150 to the support 174 or otherwise prevent the heater assembly 150 from movement within the housing 52. In one embodiment, as seen in FIG. 13, the heater assembly 150 includes an outwardly extending platform 176 having a U-shaped groove 178 in an edge thereof, wherein a cylindrical projection 180 extending upwardly from the support 174 sits within the groove 178 to prevent side-to-side movement of the platform 176.

Each of the refills 69 is inserted into and retained within the dispenser 350 by screwing the threading 274 on an outer surface of the neck 272 into a threaded portion within the dispenser 350.

Figure 14:
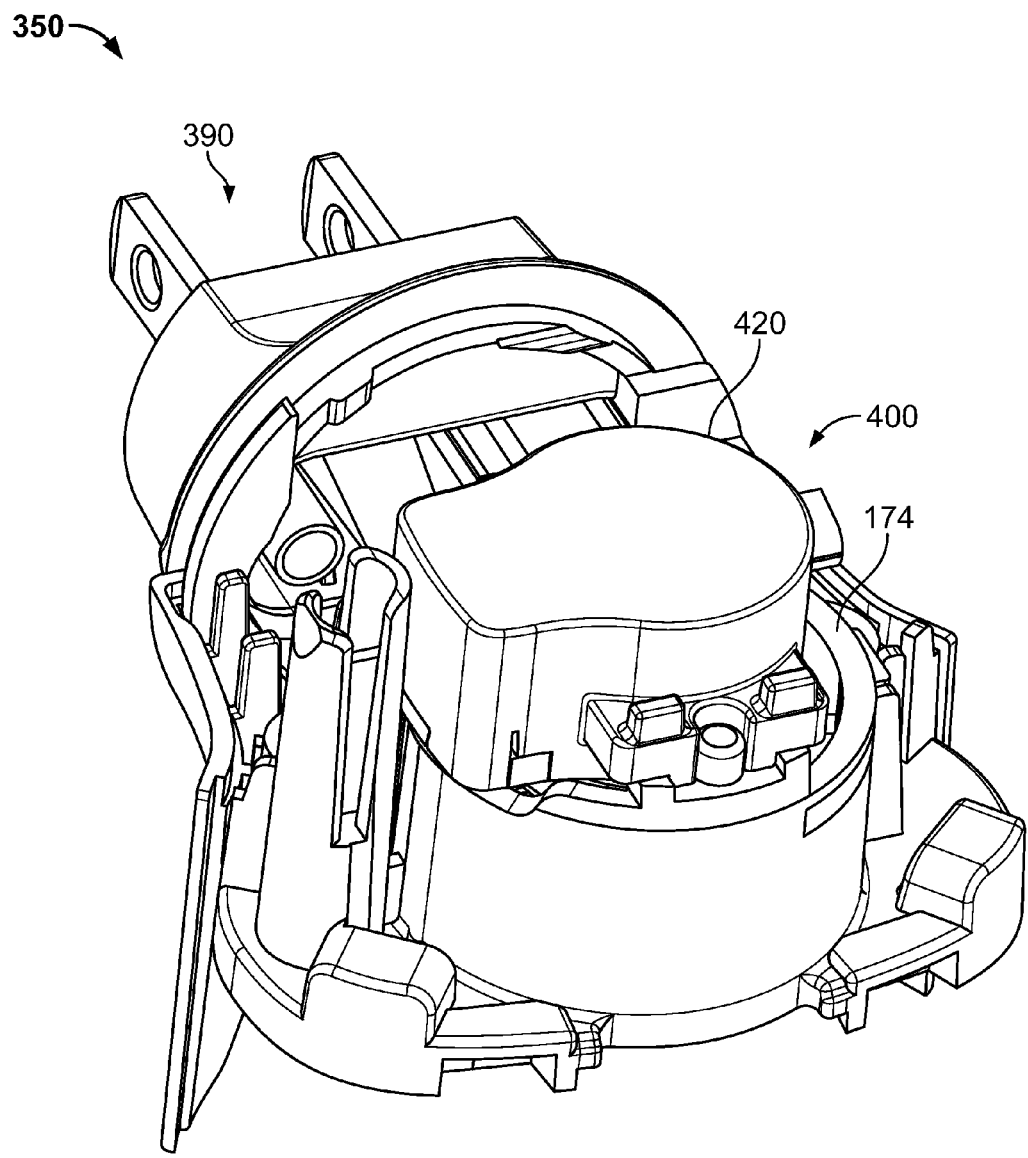
FIG. 14 is a top isometric similar to that of FIG. 13 and showing a second embodiment of a heater assembly within the volatile material dispenser of FIG. 11.
Figure 15:
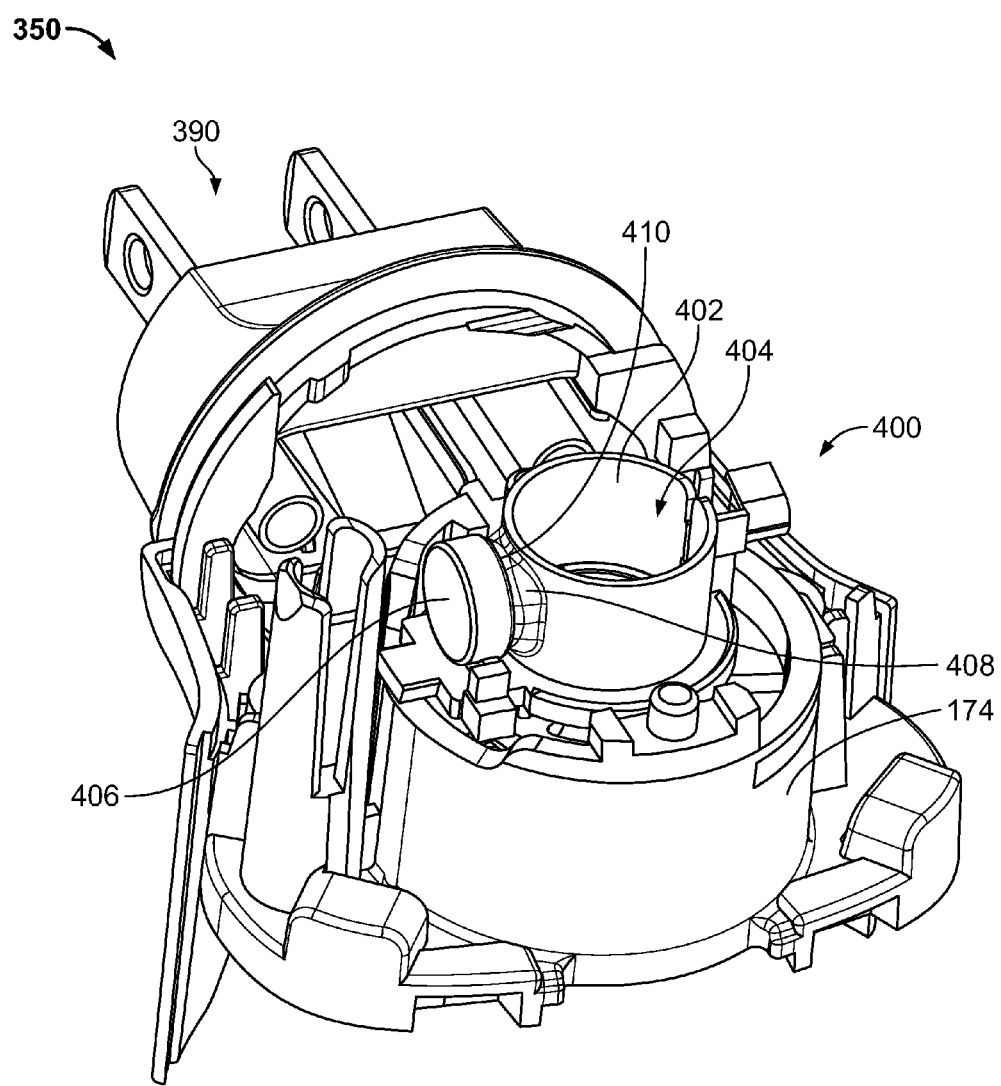
FIG. 15 is a top isometric view of the heater assembly of FIG. 14 with an insulated housing removed therefrom.

The dispenser 350 of FIGS. 11-13 is depicted in FIGS. 14 and 15 with a second embodiment of a heater assembly 400. As best seen in FIG. 15, the heater assembly 400 includes a cylindrical ring 402 having a cylindrical channel 404 therethrough, wherein the channel 404 is aligned with the cylindrical channel 175 of the support 174 such that a wick can extend through the cylindrical channel 175 and into the cylindrical channel 404 for heating, as discussed below. The cylindrical ring 402 may be made of aluminum or any other conductive material. A positive temperature coefficient (PTC) element 406 is disposed adjacent and is connected to the cylindrical ring 402 by a connecting portion 408 made of a conductive material. As seen in FIG. 15, the PTC element 406 is arranged on its side such that a side 410 of the PTC element 406 having the largest surface area is connected to the cylindrical ring 402. The PTC element 406 may be electrically connected to the plug assembly 390 in any manner known in the art.

Referring to FIG. 14, the heater assembly 400 may further include an insulated housing 420 disposed over the cylindrical ring 402 and the PTC element 406. The housing 420 encloses the cylindrical ring 402 and the PTC element 406 to retain heat within the heater assembly 400. The housing 420 may be attached to the support 174 in the same manner as described above with respect to the heater assembly 150.

During operation, the PTC element 406, which would generally operate as a point heater with heat emanating from a single point, operates to heat the cylindrical ring 402 due to the conductive nature of the connecting portion 408 and the cylindrical ring 402. The arrangement of the PTC element 406, and the cylindrical ring 402 therefore creates a cylindrical ring of heat that uniformly heats a wick disposed within the channel 404 from all sides.

Upon plugging the dispenser 350 of FIGS. 11-13 into a conventional electrical outlet, the PTC element 406 would be actuated continuously at a constant intensity level until the dispenser 350 is removed from the outlet. Optionally, the dispenser 350 may be provided with one or more switches, for example one or more of the switches disclosed with respect to the embodiment of FIGS. 1-10 or any other switch, that may allow adjustment within the dispenser 350 or on/off actuation of the dispenser 350.

Figure 16:
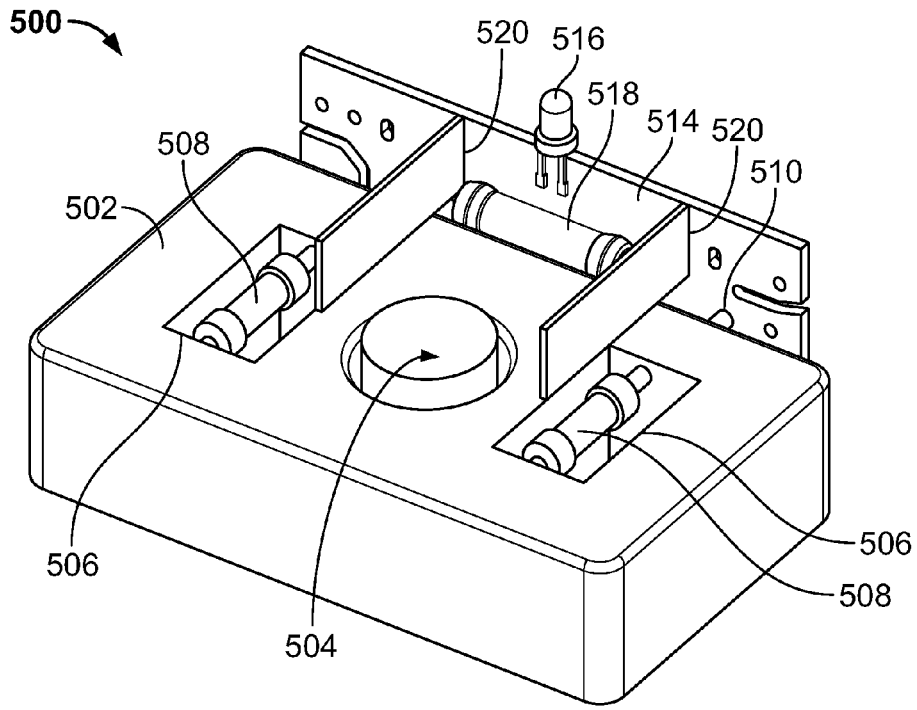
FIGS. 16, 17A, and 17B are a top isometric views of a further embodiments of heater assemblies for use within a volatile material dispenser.

A further embodiment of a heater assembly 500 that may be utilized within any of the volatile material dispensers disclosed herein is depicted in FIG. 16. In particular, the heater assembly 500 includes a heating block 502 having a central cylindrical channel 504 and cavities 506 disposed on opposite sides of the channel 504. Resistors 508 are disposed within the cavities 506 and the resistors 508 are potted in a ceramic or other conductive material to retain the resistors 508 within the cavities 506 and conduct heat throughout the heating block 502.

Resistor leads 510 extend outwardly from a first side 512 of each resistor 508 and are electrically connected to a circuit board 514. One or more LEDs 516 are connected to the circuit board 514 for providing an indicator to a user (e.g., that the dispenser is on, that a particular intensity level is selected, etc.). One or more resistors 518 extend from the circuit board 514 and are electrically connected in series with one or more LEDs 516 to act as dropping resistors to limit the current through the LEDs 516. When a refill 69 is inserted into the heating block 502, the wick extends through the cylindrical channel 502. The proximity of the one or more resistors 518 to the cylindrical channel 504 allows heat produced by the dropping resistor(s) 518 to heat the wick disposed within the channel 504, providing a boost in heat. In one embodiment, a first LED 516 is provided to indicate that the heater assembly is operating and a second LED 516 is in series with a dropping resistor 518 to provide a boost heating function, wherein illumination of the second LED 516 indicates that the boost heating function is in operation.

One or more isolating structures 520, for example walls, may be disposed between the dropping resistor(s) 518 and the resistors 508 to isolate and provide proper thermal isolation for the dropping resistor(s) 518. This thermal isolation prevents the resistors 508 from detecting the additional heat provided by the dropping resistor(s) 518 and decreasing their heat output to maintain the temperature of the system. In this manner, the dropping resistor(s) 518 truly provides a boost of heat.

While one dropping resistor 518 is depicted, any number of dropping resistors may be utilized. Also, the dropping resistors 518 may be oriented in a horizontal manner, as depicted in FIG. 16, or oriented in a vertical manner. Also, while the use of a dropping resistor 518 is disclosed in combination with one or more resistors 508, one or more dropping resistors 518 may alternatively be used with one or more PTC elements, as seen in FIG. 17A.

The additional boost of heat provided by the dropping resistor(s) 518 is done so without additional circuitry. In particular, in previous PTC-type heaters employing a change in heater temperature, the intensity or heat applied has been varied by turning the heater on and off or changing the amplitude or frequency of an electrical wave (through pulse width modulation). These previous methods involve the expense of adding a circuit board.

Figure 17A:
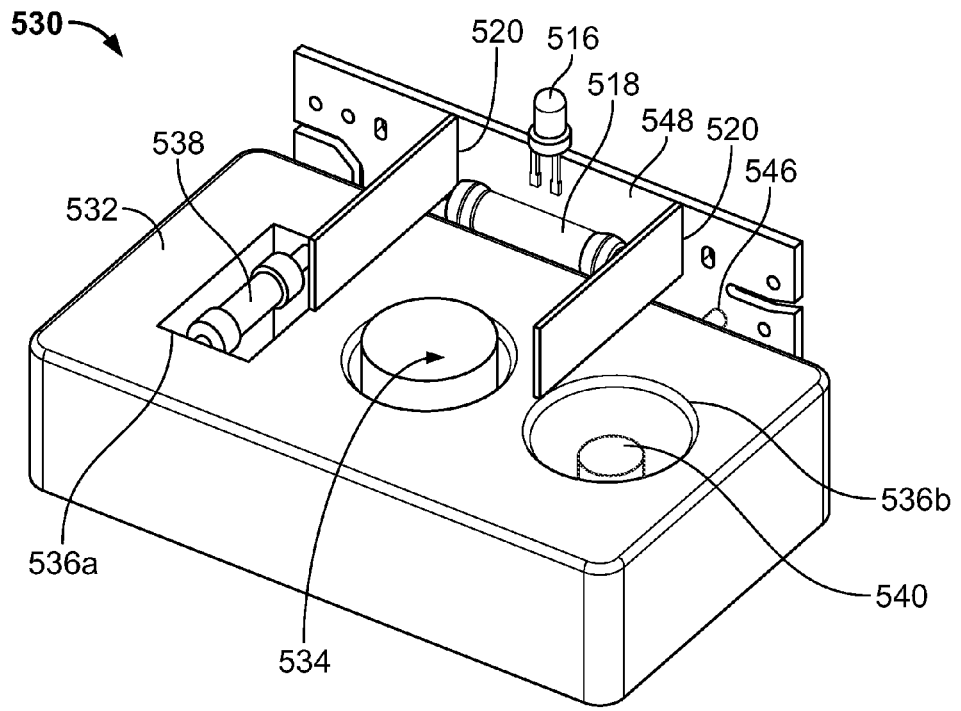

Still another embodiment of a heater assembly 530 is shown in FIG. 17A. The heater assembly 530 includes many features similar to the embodiment of FIG. 16 and includes a heating block 532 having a central cylindrical channel 534 and cavities 536a, 536b disposed on opposite sides of the channel 534. A resistor 538 is potted in ceramic or other conductive material to retain the resistor 538 within the cavity 536a and conduct heat throughout the heating block 532. The resistor 538 may be a ceramic cylinder with a resistive metal oxide coating that is deposited by sputter coating on the hollow ceramic cylinder. A spiral pattern may formed in the resistive metal oxide coating to create a desired resistance value for the resistor.

Figure 17B:
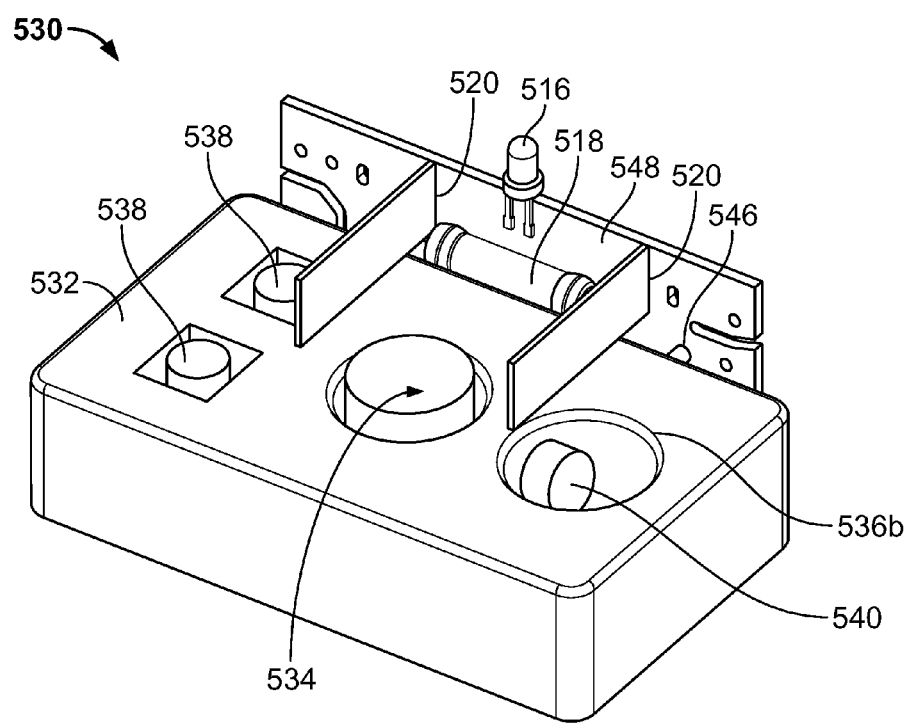

Still referring to FIG. 17A, a PTC element 540 having a generally cylindrical shape is disposed within the cavity 536b and may be oriented horizontally (see FIG. 17A) or vertically (see FIG. 17B). A conductive material may be disposed within the cavity 536b for transferring heat to the heating block 532. Optionally, the PTC element 540 may be otherwise connected to a wall 544 forming the cavity 536b by a conductive material. In a manner similar to the embodiment of FIG. 16, resistor leads 546 connect the resistor 538 and the PTC element 540 to a circuit board 548 for powering the resistor 538 and the PTC element 540.

A further embodiment of a heater assembly 560 is shown in FIG. 17B and is similar to the heater assembly 530 of FIG. 17A. In this embodiment, two resistors 538 are disposed in two cavities 536a. Optionally, two or more resistors 538 may be used and/or may be disposed in the same cavity 536a. As noted above, the PTC element 540 is also disposed vertically within the cavity 536b. In particular, the PTC element 540 is pill-shaped, includes first and second opposing flat surfaces, and a cylindrical wall. By vertical, it is meant that the PTC element 540 is oriented with one of the first and second opposing flat surfaces facing a channel adapted for insertion of the wick 534.

The heater assemblies disclosed herein may include any number of additional features known in the art. For example, if multiple resistors are utilized, the resistors may have different heating capacities.

Although a specific dispenser 50 and container 52 are described with particularity, it is contemplated the heater arrangements of the present invention may be utilized in conjunction with any type of electrical dispenser employing a heater and any type of refill and/or container. For example, dispensers useful for the present invention include, but are not limited to, the dispensers described in Belongia et al. U.S. Pat. No. 7,840,123, Varanasi et al. U.S. Pat. No. 6,968,124, Beland et al. U.S. Patent Application Publication No. 2011/0049259, Zobele U.S. Patent Application Publication No. 2005/0180736, and Pedrotti et al. U.S. Patent Application Publication No. 2003/0194225. Further, containers useful for the present invention include, but are not limited to, the containers described in U.S. Pat. No. 7,032,831, and the containers described in Gasper et al. U.S. Patent Application Publication No. 2011-0139885, both of which are owned by the same assignee as the present invention. The principles of the present invention should not be limited by a shape or size of a dispenser and/or refill.

Any of the embodiments described herein may be modified to include any of the structures or methodologies disclosed in connection with other embodiments.

Further, although directional terminology, such as front, back, top, bottom, upper, lower, etc. may be used throughout the present specification, it should be understood that such terms are not limiting and are only utilized herein to convey the orientation of different elements with respect to one another.

All documents cited in the Detailed Description are, in relevant part, incorporated herein by reference; the citation of any document is not to be construed as an admission that it is prior art with respect to the present disclosure.

INDUSTRIAL APPLICABILITY

The present invention provides various heater assemblies for a volatile material dispenser and various bottle configurations for insertion into one or more volatile material dispensers. The present invention also provides a method for operating a volatile material dispenser, wherein the method provides for a quick ramp-up in heat at the beginning of an operating cycle, different intensity levels, and/or different modes of operation.

Numerous modifications to the present disclosure will be apparent to those skilled in the art in view of the foregoing description. Accordingly, this description is to be construed as illustrative only and is presented for the purpose of enabling those skilled in the art to make and use the embodiments of the disclosure and to teach the best mode of carrying out same. The exclusive rights to all modifications which come within the scope of the appended claims are reserved.

We claim:

1. A method of emitting a volatile material from a volatile material dispenser, the method comprising the steps of:
    providing a volatile material dispenser having a housing and a heater disposed within the housing, wherein the heater includes a resistor having a particular power rating;
    programming the volatile material dispenser to include at least two intensity levels, wherein upon initiation of each of the intensity levels for an operating cycle, the resistor is operated at a first percentage of its power rating for a first period of time and
    upon selection of a first of the at least two intensity levels and after the first period of time, operating the resistor at a second percentage of its power rating for a remainder of an operating cycle; and
    upon selection of a second of the at least two intensity levels and after the first period of time, operating the resistor at the second percentage of its power rating for a second period of time and, after the second period of time, operating the resistor at a third percentage of its power rating for a remainder of an operating cycle;
    wherein the first percentage is greater than the second percentage and the second percentage is greater than the third percentage.

2. The method of claim 1, wherein the first period of time is between about 5 minutes and about 30 minutes.

3. The method of claim 2, wherein the second period of time is between about 2 hours and about 6 hours.

4. The method of claim 1, wherein the first percentage is about 99%, the second percentage is about 96%, and the third percentage is about 91%.

5. The method of claim 1, wherein the programming further includes a third intensity level and, upon selection of a third of the intensity levels, the resistor is operated at the first percentage of its power rating for the first period of time and, after the first period of time, the resistor is operated at the second percentage of its power rating for a third period of time and, after the third period of time, the resistor is operated at the third percentage of its power rating for a remainder of the operating cycle.

6. The method of claim 5, wherein the first period of time is about 10 minutes and the third period of time is about 1 hour.

7. The method of claim 5, wherein the first percentage is about 99%, the second percentage is about 96%, and the third percentage is about 91%.

8. The method of claim 1, further including the step of programming the volatile material dispenser to include two operating cycles for selection by a user, a first of the operating cycles including an 8 hour on period and a 16 hour off period and a second of the operating cycles including a 12 hour one period and a 12 hour off period.

9. The method of claim 8, further including the step of continuously cycling through the selected operating cycle until a new operating cycle is selected or the dispenser is deactivated.

* * * * *